(12) United States Patent
June et al.

(10) Patent No.: US 7,172,869 B2
(45) Date of Patent: Feb. 6, 2007

(54) METHODS FOR TRANSFECTING T CELLS

(75) Inventors: Carl H. June, Merion Station, PA (US); Thompson B. Craig, Philadelphia, PA (US); Suil Kim, San Francisco, CA (US)

(73) Assignees: The United States of America as represented by the Secretary of the Navy, Washington, DC (US); The Regents of the University of Michigan, Ann Arbor, MI (US)

( * ) Notice: Subject to any disclaimer, the term of this patent is extended or adjusted under 35 U.S.C. 154(b) by 133 days.

(21) Appl. No.: 10/828,481

(22) Filed: Apr. 20, 2004

(65) Prior Publication Data

US 2004/0203155 A1 Oct. 14, 2004

Related U.S. Application Data

(63) Continuation of application No. 10/658,787, filed on Sep. 9, 2003, which is a continuation of application No. 08/475,136, filed on Jun. 7, 1995, now Pat. No. 6,692,964, which is a continuation-in-part of application No. 08/435,095, filed on May 4, 1995, now abandoned.

(51) Int. Cl.
| | |
|---|---|
| *C12Q 1/68* | (2006.01) |
| *C12N 5/12* | (2006.01) |
| *C12N 5/00* | (2006.01) |
| *A61K 48/00* | (2006.01) |

(52) U.S. Cl. .............................. 435/6; 435/6; 435/325; 435/375; 424/93.21

(58) Field of Classification Search ..................... None
See application file for complete search history.

(56) References Cited

U.S. PATENT DOCUMENTS

| | | | | |
|---|---|---|---|---|
| 5,272,082 A | * | 12/1993 | Santoli et al. ............... | 435/325 |
| 5,399,346 A | * | 3/1995 | Anderson et al. ......... | 424/93.21 |
| 5,443,983 A | * | 8/1995 | Ochoa et al. ............... | 435/325 |
| 5,733,543 A | * | 3/1998 | Nabel et al. .............. | 424/93.21 |
| 5,738,852 A | * | 4/1998 | Robinson et al. ........ | 424/199.1 |
| 5,827,642 A | * | 10/1998 | Riddell et al. .................. | 435/2 |
| 5,858,358 A | * | 1/1999 | June et al. ............... | 424/130.1 |
| 6,692,964 B1 | | 2/2004 | June et al. | |

2004/0087025 A1 5/2004 June et al.

FOREIGN PATENT DOCUMENTS

| | | |
|---|---|---|
| WO | WO-90/05541 | 5/1990 |
| WO | WO-94/12196 | 6/1994 |
| WO | WO-94/29436 | 12/1994 |
| WO | WO 95/01447 | 1/1995 |
| WO | WO-95/03408 | 2/1995 |
| WO | WO-95/33823 | 12/1995 |
| WO | WO-95/34320 | 12/1995 |
| WO | WO-96/01122 | 1/1996 |
| WO | WO-96/02646 | 2/1996 |
| WO | WO-96/06942 | 3/1996 |

OTHER PUBLICATIONS

Report and Recommendations of the Panel to Assess the NIH Investment in Research on Gene Therapy, Dec. 1995 pp. 21-22.*
Verma IM, Somia N. Gene therapy—promises, problems and prospects. Nature. 1997; 389:239-42.*
Fundamental Immunology, Second Edition, edited by WE Paul, Raven Press Ltd., New York ch. 13 and 15, 1989.*
Pullen, AM. Superantigens. in: Encyclopedia of Immunology, IM Roitt, ed. Academic Press, New York, 1993.*
Fundamental Immunology, Second Edition, ed. by WE Paul, Raven Press Ltd., New York, ch. 13, pp. 359-384.
Pullen, AM. Superantigens in Encyclopedia of Immunology, IM Rotill, ed. Academic Press, New York, 1993, pp. 1406-1408.
Van Senventer et al., Costimulation of T cell receptor/ CD3-mediated activation of resting human CD4+ cells by leukocyte funcloin-associated antigen-1 ligna inercellular cell adhesion molule-1 involves prolonged inolsito phosphol. J. Immunol. 149:3872-3880.
U.S. Appl. No. 10/828,481, filed Apr. 20, 2004, June et al.
Culver et al., "In Vivo Expression and Survival of Gene-Modified T Lymphocytes in Rhesus Monkeys," Human Gene Therapy, 1:399-410 (1990).
U.S. Appl. No. 10/658,787, filed Sep. 9, 2003, June et al.
Cann et al., "High Efficiency Transfection of Primary Human Lymphocytes and Studies of Gene Expression," Oncogene, 3:122-128 (1988).
Coghlan, "Gene Dream Fades Away" New Scientist, 148: 14-15 (1995).

(Continued)

*Primary Examiner*—Janet L. Epps-Ford
*Assistant Examiner*—Maria Leavitt
(74) *Attorney, Agent, or Firm*—Wilmer Cutler Pickering Hale and Dorr, LLP

(57) ABSTRACT

A method for transfecting T cells with a nucleic acid molecule comprising a gene such that the gene is expressed in the T cells is described. The T cells are stimulated and proliferating prior to introduction of the nucleic acid molecule.

51 Claims, 13 Drawing Sheets

OTHER PUBLICATIONS

Crystal, "Transfer of Genes to Humans: Early Lessons and Obstacles to Success" Science, 270:404-410 (1995).

Fauser, "Long-Term Expression of Gene Introduction into Normal Human T-Lymphocytes by Retroviral-Mediated Gene Transfer," Journal of Cellular Biochemistry, 45:353-358 (1991).

Finer et al., "kat: A High-Efficiency Retroviral Transduction System for PRimary HUman T Lymphocytes," Blood, 83(1):43-50 (1994).

Guba et al., "Interleukin-3 Gene Induction in Normal Human T Cells Via Stimulation of CD3 and CD28," Clinical Research, 37(4) (1989).

Gunzburg et al., "Virus Vector Design in Gene Therapy" Molecular Medicine Today, 410-417 (1995).

Lowenthal et al., "Tumor Necrosis Factor $\alpha$ Induces Proteins that Bind Specifically to kB-like Enhancer Elements and Regulate Interleukin 2 Receptor $\alpha$-chain Gene Expression in Primary Human T Lymphocytes," PNAS USA, 86:2331-2335 (1989).

Mastrangelo et al. "Gene Therapy for Human Cancer: An essay for Clinicians" Seminars In Oncology, 23(1):4-21 (1996).

Novak et al., "In Vitro Transfection of Fresh Thymocytes and T Cells Shows SUbset-Specific Expression of Viral Promoters," Molecular and Cellular Biology, 12:1515-1527 (1992).

Park et al., "Transcriptional Regulation of Interleukin 3 (IL3) in Primary Human T Lymphocytes," Journal of Biological Chemistry, 268(9):6299-6308 (1993).

Philip et al., "Efficient and Sustained Gene Expression in Primary T Lymphocytes and Primary and Cultured Tumor Cells Mediated by Adeno-Associated Virus Plasmid DNA Complexed to Cationic Liposomes," Molecular and Cellurlar Biology, 14:2411-2418 (1994).

Tiberghein et al., "Ganciclovir Treatment of Herpes Simplex Thymidine Kinase-Transduced Primary T Lymphocytes: An Approach for Specific In Vivo Donor T-Cell Depletion After Bone Marrow Transplantation?" Blood, 84(4):1333-1341 (1994).

Sambucetti et al. "NF-$_\kappa$B activation of the cytomegalovirus enhancer is mediated by a viral transactivator and by T cell stimulation," The EMBO Journal, 1989, pp. 4251-4258, vol. 8, No. 13.

Guba et al., "Interleukin-3 Gene Induction in Normal Human T Cells Via Stimulation of CD3 and CD28," Clinical Research, 37(4): 902A (1989).

* cited by examiner

Resting: Day 1
%G$_0$ 98.0
%G$_1$ 0.5
%S/G$_2$M 1.3
3H-TdR-Incorporation (cpm/E3)
0.29 ± 0.07

αCD3/αCD28: Day 3
%G$_0$ 6.3
%G$_1$ 46.6
%S/G$_2$M 47.0
3H-TdR-Incorporation (cpm/E3)
59.9 ± 3.4

MED: Day 6
%G$_0$ 5.2
%G$_1$ 45.7
%S/G$_2$M 48.7
3H-TdR-Incorporation (cpm/E3)
52.3 ± 7.0

PDBU/IONO: Day 6
%G$_0$ 5.4
%G$_1$ 46.2
%S/G$_2$M 48.1
3H-TdR-Incorporation (cpm/E3)
35.2 ± 2.1

US 7,172,869 B2

METHODS FOR TRANSFECTING T CELLS

RELATED APPLICATIONS

This application is a continuation of U.S. patent application Ser. No. 10/658,787, filed Sep. 9, 2003, which is a continuation of U.S. patent application Ser. No. 08/475,136, filed Jun. 7, 1995, now U.S. Pat. No. 6,692,964, which in turn is a continuation-in-part of U.S. patent application Ser. No. 08/435,095, filed May 4, 1995, now abandoned, the entire contents of each of which are incorporated herein by reference.

GOVERMENT SUPPORT

Work described herein was supported in part by NMRDC grant 61153N AE.4120.001.1402. The U.S. government therefore may have certain rights in the invention.

BACKGROUND

The expression of exogenous DNA in eukaryotic cells permits the study of a broad array of biological topics ranging from the regulation of gene expression to the treatment of disease by gene transfer-based therapies. A number of methods for gene transfer into mammalian cells have evolved. These include in vivo and in vitro infection with cloned retroviral vectors (Shimotohno, K., and Temin, H. M. (1981) Cell 26:67–77; Cone, R. D., and Mulligan, R. C. (1984) Proc. Natl. Acad Sci USA 81:6349–6353; Dubensky, T. W., Campbell, B. A., and Villareal, L. P. (1984) Proc. Natl. Acad Sci. USA 81:7529–7533; Seeger, C., Ganern, D. and Varmus, H. E. (1984) Proc. Natl. Acad Sci. USA 81:5849–5852), coprecipitation of DNA with calcium phosphate (Chu, G., and Sharp, P. (1981) Gene 13:197–202; Benvenisty, N., and Reshef, L. (1986) Proc. Natl. Acad Sci. USA 83:9551–9555), encapsulation of DNA in liposomes (Feigner, P. L., and Ringold, G. M. (1989) Nature 337: 387–388; Kaneda, Y., Iwai, K., and Uchida, T. (1989) Science 243:375–378), direct injection of plasmid DNA (Wolff, J. A., Malone, R. W., Williams, P., Chong, W., Acsadi, G., Jani, A., and Felgner, P. L. (1990) Science 247:1465–1468), DEAE-dextran (McCutchan, J. H., and Pagano, J. S. (1968) J. Natl. Cancer Inst. 41:351–357), electroporation (Neumann, E., Schaefer-Ridder, M., Wang, Y., and Hofschneider, P. H. (1982) EMBO J. 1:841–845; Cann, A. J., Koyanagi, Y., and Chen, I. S. Y. (1988) Oncogene 3:123–128), and DNA-coated particle bombardment of cells and tissues (Yang, N-S., Burkholder, J., Roberts, B., Martinell, B., and McCabe, D. (1990) Proc. Natl. Acad Sci. USA 87:9568–9572).

Although transfection of numerous cell types with an exogenous nucleic acid molecule containing a gene results in efficient expression of the exogenous gene, primary T lymphocytes, e.g. peripheral blood T lymphocytes obtained from an individual, have been found to be refractory to transfection and expression of exogenous DNA Primary T lymphocytes also have been found to be refractory to expression of the introduced nucleic acid when first stimulated to proliferate. Thus, a system that allows for efficient introduction of exogenous DNA into primary T cells and expression of the exogenous DNA in the T cell is still needed.

SUMMARY

The present invention provides an improved method for transfecting T cells with a nucleic acid molecule containing a gene such that expression of the gene in the T cells is enhanced as compared to classic transfection techniques. The method of the invention is particularly useful for transfecting primary T cells which are refractory to classical transfection techniques. The method involves contacting a proliferating T cell with one or more agents which stimulate the proliferating T cell prior to introducing the nucleic acid molecule into the T cell. In one embodiment of the invention, the T cell is stimulated with a combination of a first agent which provides a primary activation signal to the T cell and a second agent which provides a costimulatory signal. The method of the invention has numerous applications, in particular for gene therapy.

DETAILED DESCRIPTION

Figure 1:
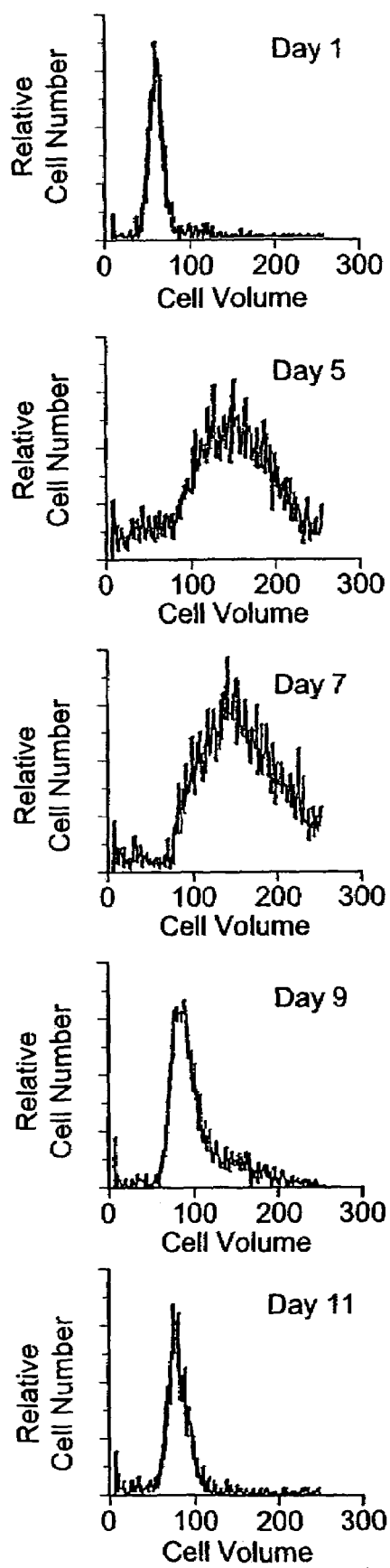
FIG. 1 represents graphically the relative cell number and cell volume of CD28$^+$ T cells at day 1, 5, 7, 9, and 11 following stimulation (at day 0) with anti-CD3 coated plates and anti-CD28 at 1 μg/ml.

The present invention provides an improved method for transfecting a T cell with a nucleic acid molecule comprising a gene such that the gene is expressed in the T cell. The method of the invention comprises contacting a proliferating T cell with at least one agent which stimulates the proliferating T cell prior to introducing the nucleic acid molecule into the T cell, such that the gene is expressed in the T cell.

The method of the invention is based, at least in part, on the observation that transfection of primary T cells with a nucleic acid comprising a gene results in poor expression of the gene unless the primary T cells are proliferating and, furthermore, are stimulated with stimulatory agents, such as agents which induce a primary activation signal and a costimulatory signal in the T cells. The T cells are preferably contacted with the stimulatory agents about 10 hours prior to introducing the nucleic acid into the T cells. Thus, significant expression of an exogenous gene can be achieved in T cells by stimulating proliferating T cells prior to introducing a nucleic acid comprising the gene into the T cells.

Thus, the invention provides an improved method for transfecting T cells with a nucleic acid molecule comprising a gene such that the gene is expressed in the T cells. The improvement provided by the methods of the invention over classical T cell transfection methods involves contacting the T cell with a stimulatory agent prior to (eg. several hours) introducing the nucleic acid molecule into proliferating T cells. The method of the invention allows for much higher expression of the gene introduced into the T cells than conventional transfection techniques. The method of the invention is particularly useful for introducing and expressing a gene of interest into primary T cells. Thus, in a specific embodiment of the method, T cells are obtained from a subject, transfected in vitro with a nucleic acid molecule according to the methods of the invention, and readministered to the host. The gene of interest can be a gene encoding a protein, or a gene encoding a functional RNA molecule, such as an antisense molecule or a ribozyme. The gene of interest can encode any protein of interest, including proteins that protect the T cells, proteins that are toxic to the T cells, or proteins that are secreted from the T cells to effect other cells. Thus, the method of the invention is applicable to, for example, gene therapy, alteration of T cell function and production of proteins in T cells.

1. T Cells That Can Be Transfected According to the Method of the Invention

The invention involves a method for transfecting a T cell with a nucleic acid molecule comprising a gene, such that the gene is expressed in the T cell. The term "T cell" refers to T lymphocytes as defined in the art and is intended to include thymocytes, immature T lymphocytes, mature T lymphocytes, resting T lymphocytes, or activated T lymphocytes. The T cells can be $CD4^+$ T cells, $CD8^+$ T cells, $CD4^+ CD8^+$ T cells, or $CD4^- CD8^-$ T cells. The T cells can also be T helper cells, such as T helper 1 (Th1) or T helper 2 (Th2) cells. T cells that differ from each other by at least one marker, such as CD4, are referred to herein as "subsets" of T cells.

The T cells can be a purified population of T cells, or alternatively the T cells can be in a population with cells of a different type, such as B cells and/or other peripheral blood cells. The T cells can be a purified population of a subset of T cells, such as $CD4^+$ T cells, or they can be a population of T cells comprising different subsets of T cells. In another embodiment of the invention, the T cells are T cell clones that have been maintained in culture for extended periods of time. T cell clones can be transformed to different degrees. In a specific embodiment, the T cells are a T cell clone that proliferates indefinitely in culture.

In a preferred embodiment of the invention, the T cells are primary T cells. The language "primary T cells" is intended to include T cells obtained from an individual, as opposed to T cells that have been maintained in culture for extended periods of time. Thus, primary T cells are preferably peripheral blood T cells obtained from a subject. A population of primary T cells can be composed of mostly one subset of T cells. Alternatively, the population of primary T cells can be composed of different subsets of T cells.

The T cells can be from a healthy individual, or alternatively the T cells maybe from an individual affected with a condition. The condition can be an infectious disease, such as a condition resulting from a viral infection, a bacterial infection or an infection by any other microorganism. In a specific embodiment, the T cells are from an individual infected with a human immunodeficiency virus (HIV). In yet another embodiment of the invention, the T cells are from a subject suffering from or susceptible to an autoimmune disease. The T cells can be of human origin, murine origin or any other mammalian species.

According to the method of the invention, the nucleic acid molecule is introduced into T cells that are actively proliferating. T cells can be stimulated to proliferate by contacting the T cells with a variety of agents, such as a combination of agents providing a primary activation signal and a costimulatory signal to T cells. Agents that can be used to stimulate T cells to proliferate are well known in the art and are described below, in Section 2. T cells that are stimulated to proliferate are characterized by cellular enlargement, clumping, and acidification of the culture medium. Thus, T cell proliferation can be evidenced by, for example, examining the size or measuring the volume of the T cells, such as with a Coulter Counter. A resting T cell has a mean diameter of about 6.8 microns. Following the initial activation and stimulation the T cell mean diameter will increase to over 12 microns by day 4 and begin to decrease by about day 6. Moreover, T cell proliferation can be assessed by standard techniques known in the art, such as tritiated thymidine uptake.

2. Stimulatory Agents

The method of the invention involves contacting proliferating T cells with at least one stimulatory agent prior to introducing the nucleic acid molecule into the proliferating T cell. The term "stimulatory agent" is intended to include agents which provide a signal to the T cell, such that the level of expression of the gene comprised in the nucleic acid molecule transfected into the T cell is higher when the T cell is contacted with the stimulatory agent prior to introducing the nucleic acid molecule into the T cell, than in T cells not contacted with the stimulatory agent prior to introducing the nucleic acid molecule.

In a specific embodiment of the invention, the stimulatory agent is an agent which provides a primary activation signal to a T cell. The language "primary activation signal" is intended to include signals, typically triggered through the TCR/CD3 complex, that induce activation of T cells. Activation of a T cell is intended to include modifications of a T cell, such that the T cell is induced to proliferate and differentiate upon receiving a second signal, such as a costimulatory signal. In a specific embodiment, the primary activation signal is provided by an agent which contacts the T cell receptor or the CD3 complex associated with the T cell receptor. In a preferred embodiment, the agent is an antibody reactive against CD3, such as the monoclonal antibody OKT3 (available from the American Type Culture Collection, Rockville, Md.; No. CRL 8001). In another embodiment of the invention, the stimulating agent is an agent that stimulates the CD2 complex on T cells, such as a combination of antibodies, e.g. T11.3+T11.1 or T11.3+T11.2 (see e.g., Meuer, S. C. et al. (1984) *Cell* 36:897–906).

In a preferred embodiment of the invention, the T cells are stimulated with a combination of agents that stimulate both a primary activation signal and a costimlulatory signal in the T cell. The term "costimulatory agent" is intended to include agents which provide a costimulatory signal in T cells, such that a T cell that has received a primary activation signal (e.g. an activated T cell) is stimulated to proliferte or to secrete cytokines, such as IL-2, ILA, or interferon-γ. In a specific embodiment, the costimulatory agent interacts with CD28 or CTLA4 molecules on the surface of the T cells. In an even more specific embodiment, the costimulatory signal is a ligand of CD28 or CTLA4, such as a B-lymphocyte antigen B7-1 or B7-2. The language "stimulatory form of a natural ligand of CD28" is intended to include B7-1 and B7-2 molecules, fragments thereof, or modifications thereof, which are capable of providing costimulatory signals to the T cells. Stimulatory forms of natural ligands of CD28 can be identified by, for example, contacting activated peripheral blood lymphocytes with a form of a natural ligand of CD28 and performing a standard T cell proliferation assay. Thus, a stimulatory form of a natural ligand of CD28 is capable of stimulating proliferation of the T cells. Stimulatory forms of natural ligands of CD28/CTLA4 are described, for example, in PCT Publication No. WO 95/03408.

Other agents that can be used to stimlulate T cells prior to introducing a nucleic acid molecule into the T cell include agents that stimulate one or more intracellular signal transduction pathways involved in T cell activation and/or costimulation. In a preferred embodiment of the invention, the stimulatory agent is a calcium ionophore, such as ionomycin or A23187. Alternatively, the stimulatory agent can be an agent which stimulates protein kinase C, such as a phorbol ester. A preferred phorbol ester is phorbol-12,13-dibutyrate. In an even more preferred embodiment of the invention, T cells are contacted with a combination of a calcium ionophore and a phorbol ester prior to transfection with a nucleic acid molecule. The stimulatory agent can also be an agent which activates protein tyrosine kinases. A preferred agent that stimulates protein tyrosine kinases is pervanadate (O'Shea, J. J., et al. (1992) *Proc. Natl. Acad Sci. USA* 89:10306).

In yet another embodiment of the invention, the stimulatory agent is a polyclonal activator. Polyclonal activators include agents that bind to glycoproteins expressed on the plasma membrane of T cells and include lectins, such as phytohemaglutinin (PHA), concanavalin (Con A) and pokeweed mitogen (PWM).

By providing a clone a specific activation signal, it is possible to selectively transfect only a certain clone of T cells in a population of T cells. Specific activation of a T cell clone can be accomplished, for example, using a specific antigen presented by an antigen-presenting cell.

In yet another embodiment of the method, the stimulatory agent is a lymphokine, such as IL-2. The lymphokine is preferably used in combination with another agent, such as an agent which provides a primary activation signal to the T cell, for stimulating T cells. Thus, in a preferred embodiment of the invention, T cells are contacted with a combination of an agent which provides a primary activation signal to the T cells (e.g., an anti-CD3 antibody) and an effective amount of IL-2, prior to transfecting the T cells with a nucleic acid molecule, such that the nucleic acid molecule is expressed in the T cells.

Other stimulating agents that can be used include super-antigens. The term "super-antigen" as defined herein is intended to include bacterial enterotoxins, or other bacterial proteins capable of stimulating proliferation of T cells. Super-antigens include staphylococcal enterotoxins (SE), such as SEA, SEB, SEC, SED, and SEE. Super-antigens can also be of viral origin, such as retroviral super-antigens.

Additional agents that are capable of stimulating T cells, either alone or in combination with other agents, that may be identified using T cell stimulation assays as known in the art or described herein are also within the scope of the invention. For stimlulating T cells prior to introduction of a nucleic acid molecule into the T cells, any combination of the above described agents can be used.

The stimulating agents can be used in solution, or attached to a solid surface. The solid surface can be, for example, the surface of a tissue culture dish or a bead. Depending on the nature of the stimulatory agent, linkage to the solid surface can be performed by methods well known in the art. For example, proteins can be chemically crosslinked to the cell surface using commercially available crosslinking reagents (Pierce, Rockford Ill.) or immobilized on plastic by overnight incubation at 4° C. If several agents are used for stimulation of the T cells, some agents may be in solution and some agents may be attached to a solid support. In a preferred embodiment, the T cells are stimulated with a combination of solid phase coupled anti-CD3 antibody and soluble anti-CD28 antibody.

The specific doses of stimulatory agent(s) to be added to the T cells will vary with the type of stimulating agent. Typically, the stimulating agents are used at the same doses at which they are used for stimulating T cells to proliferate and secrete cytokines, as described in the art.

3. Protocols For Stimulation Prior to Transfection

In a specific embodiment of the invention, T cells are contacted with the stimulatory agent prior to introducing the nucleic acid molecule comprising the gene into the T cells. In a preferred embodiment of the invention, the T cells are contacted with the stimulatory agent at least about 2 hours before introducing the nucleic acid molecule into the T cells. In another embodiment of the invention, the T cells are contacted with the stimulatory agent at least about 4 hours before introducing the nucleic acid molecule into the T cells. In another embodiment of the invention, the T cells are contacted with the stimulatory agent at least about 6 hours before introducing the nucleic acid molecule into the T cells. In another embodiment of the invention, the T cells are contacted with the stimulatory agent at least about 8 hours before introducing the nucleic acid molecule into the T cells. In other embodiments, the T cells are contacted with the stimulatory agent at most about 2 hours before transfection at most about 4 hours before transfection, at most about 6 hours before transfection, at most about 8 hours before transfection, at most about 10 hours before transfection, at most about 12 hours before transfection, at most about 14 hours before transfection, at most about 16 hours before transfection, at most about 18 hours before transfection, at most about 20 hours before transfection, at most about 22 hours before transfection, at most about 24 hours before transfection.

In an even more preferred embodiment of the invention, the T cells are contacted with a nucleic acid molecule between about 1 hour and 24 hours prior to introducing the nucleic acid molecule into the T cells. In a most preferred embodiment of the invention, proliferating T cells are contacted with at least one stimulatory agent between about 5 and 15 hours, such as about 10 hours prior to transfecting a nucleic acid molecule comprising a gene of interest.

In one embodiment of the method, proliferating T cells are contacted with at least one stimulatory agent and further transfected with the nucleic acid molecule. In another embodiment of the method, the non-proliferating T cells are stimulated to proliferate, then contacted with at least one stimulatory agent prior to being transfected according to the method of the invention. Non-proliferating T cells can be stimulated to proliferate using agents well known in the art, such as those described above, under the section "Stimulatory Agents". Preferred agents include a combination of an agent which provides a primary activation signal and an agent which provides a costimulatory signal. Other preferred combinations of agents for stimulating proliferation of T cells include combinations of a to phorbol ester and a calcium ionophore, or PMA and IL-2.

According to a most preferred embodiment of the method for transfecting primary T cells, resting primary T cells are first contacted with at least one agent which stimulates proliferation of T cells, such as a combination of a calcium ionophore and a phorbol ester. At a time between approximately 3 and 8 hours, preferably approximately 5 hours, following induction of T cell proliferation, the proliferating T cells are contacted with at least one agent which stimulates the T cells. Finally, between 2 and 15 hours, preferably about 10 hours, following contact with the stimulatory agent, the T cells are transfected with a nucleic acid molecule comprising a gene of interest, such that the gene is expressed in the T cells. In another embodiment, the T cells are further contacted with agents that stimulate the T cells after transfection of the T cells.

To obtain primary T cells from a subject, peripheral blood mononuclear cells can be isolated from a subject and purified by density gradient centrifugation, e.g., Ficoll/Hypaque. In a specific embodiment, the purified peripheral blood cells are then transfected with a nucleic acid molecule according to the method of the invention. In other embodiments of the method, the peripheral blood mononuclear cells are further enriched in specific cell-types prior to being transfected. Monocytes can be depleted, for example, by adherence on plastic. If desired, the $CD4^+$ T cell population can further be enriched by separation from residual monocytes, B cells, NK cells and $CD8^+$ T cells using monoclonal antibody (mAb) and anti-mouse-Ig coated magnetic beads using commercially available mAbs (such as anti-CD14 (Mo2), anti-CD11b (Mo1), anti-CD20 (B1), anti-CD16 (3G8) and anti-CD8 (7PT 3F9) mAbs). The method of the invention can also be applied to subsets of $CD4^+$ T cells, such as $CD4^+CD45RA^+$ (naive $CD4^+$ T cells) and $CD4^+CD45RO^+$ (memory T cells) T cell subsets. These can be prepared as described above, with the additional use of anti-CD45RO antibody. (UCHLI) for the preparation of the $CD4^+$ $CD45RA^+$ cells and the addition of anti-CD45RA antibody (2H4) for the preparation of the $CD4^+CD45RO^+$ T cells.

The efficiency of the purification can be analyzed by flow cytometry (Coulter, EPICS Elite), using anti-CD3, anti-CD4, anti-CD8, anti-CD14 mAbs, or additional antibodies that recognize specific subsets of T cells, followed by fluorescein isothiocyanate conjugated goat anti mouse immunoglobulin (Fisher, Pittsburgh, Pa.) or other secondary antibody.

In a preferred embodiment of the invention, the method of the invention further comprises stimulating the T cells to expand in vitro after transfection of the T cells. T cells can be stimulated to expand in vitro as described in the Examples section. In a specific embodiment, T cells are incubated with an agent which provides a primary activating signal, such as anti-CD3 and an agent which provides a costimulatory signal, such as an anti-CD28 antibody. Two days later, the cells are diluted with fresh medium and the agent providing the costimulatory agent is added to the culture. The T cells are then counted, sized, and diluted with fresh medium every two days until the sizing distribution shifted nearly back to a resting cell profile (at about 10 days). The T cells can then be restimulated with the agent which provides a primary activating signal and an agent which provides a costimulatory signal. T cells sizing and counting can be performed using a Coulter Counter, as described herein.

In an even more preferred embodiment, the T cells are primary T cells. Thus, T cells can be obtained from a subject, transfected according to the method of the invention, and expanded in vitro. In another embodiment of the invention, the transfected and expanded T cells are readministered to the subject. It may be preferable to further purify the T cells prior to administering into the subject, such as by gradient centrifugation.

4. Transfection of the T Cells

The invention pertains to methods for transfecting T cells with a nucleic acid comprising a gene, such that the gene is expressed in the T cells. The language "transfecting T cells" is intended to include any means by which a nucleic acid molecule can be introduced into a T cell. The term "transfection" encompasses a variety of techniques useful for introduction of nucleic acids into mammalian cells including electroporation, calcium-phosphate precipitation, DEAE-dextran traunent, lipofection, microinjection, and viral infection. Suitable methods for transfecting mammalian cells can be found in Sambrook et al. (*Molecular Cloning: A Laboratory Manual, 2nd Edition*, Cold Spring Harbor Laboratory press (1989)) and other laboratory textbooks.

In a preferred embodiment of the invention, the nucleic acid molecule encoding a gene of interest is introduced into a T cell using a viral vector. Such viral vectors include, for example recombinant retroviruses, adenovirus, adeno-associated virus, and herpes simplex virus-1. Retrovirus vectors and adeno-associated virus vectors are generally understood to be the recombinant gene delivery system of choice for the transfer of exogenous genes in vivo, particularly into humans. Alternatively they can be used for introducing exogenous genes ex vivo into T cells. These vectors provide efficient delivery of genes into T cells, and the transferred nucleic acids are stably integrated into the chromosomal DNA of the host cell. A major prerequisite for the use of retroviruses is to ensure the safety of their use, particularly with regard to the possibility of the spread of wild-type virus in the cell population. The development of specialized cell lines (termed "packaging cells") which produce only replication-defective retrovirus has increased the utility of retroviruses for gene therapy, and defective retroviruses are well characterized for use in gene transfer for gene therapy purposes (for a review see Miller, A. D. (1990) *Blood* 76:271). Thus, recombinant retrovirus can be constructed in which part of the retroviral coding sequence (gag, pol, env) is replaced by a gene of interest rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP; pWE and pEM which are well known to those skilled in the art. Examples of suitable packaging virus lines for preparing both ecotropic and amphotropic retroviral systems include ψCrip, ψCre, ψ2 and ψAm.

Furthermore, it has been shown that it is possible to limit the infection spectrum of retroviruses and consequently of retroviral-based vectors, by modifying the viral packaging proteins on the surface of the viral particle (see, for example PCT publications WO93/25234 and WO94/06920). For instance, strategies for the modification of the infection spectrum of retroviral vectors include: coupling antibodies specific for cell surface antigens to the viral env protein (Roux et al. (1989) *PNAS* 86:9079–9083; Julan et al. (1992) *J. Gen Virol* 73:3251–3255; and Goud et al. (1983) *Virology* 163:251–254); or coupling cell surface receptor ligands to the viral env proteins (Neda et al. (1991) *J. Biol Chem*

266:14143–14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). Thus, in a specific embodiment of the invention, viral particles containing a nucleic acid molecule containing a gene of interest operably linked to appropriate regulatory elements, are modified for example according to the methods described above, such that they can specifically target subsets of T cells. For example, the viral particle can be coated with antibodies to surface molecule that are specific to certain types of T cells. In particular, it is possible to selectively target $CD4^+$ T cells by linking to the viral particle antibodies that recognize the CD4 molecule on the T cell. Thus, indection of $CD4^+$ T cells will occur preferentially over infection of $CD8^+$ T cells. This method is particularly useful when only specific subsets of T cells are desired to be transfected. Additional retroviral systems for introducing and expressing a nucleic acid molecule comprising a gene of interest in T cells, including primary T cells, are described in Kasid, A. et al. (1990) *Proc. Natl. Acad Sci. USA.* 87, 473; Morecki, S. et al. (1991) *Cancer Immunol. Immunother.* 32, 342; Culver, K et al. (1991) *Proc. Natl. Acad. Sci. U.S.A.* 88, 3155; and Finer, M. H. et al. (1994) *Blood*, 83, 43.

Another viral gene delivery system useful in the present invention utilitizes adenovirus-derived vectors. The genome of an adenovirus can be manipulated such that it encodes and expresses a gene product of interest but is inactivated in terms of its ability to replicate in a normal lytic viral life cycle. See for example Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses can be advantageous in certain circumstances in that they are not capable of infecting nondividing cells. Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited, supra; Haj-Ahmand and Graham (1986) *J. Virol.* 57:267). Most replication-defective adenoviral vectors currently in use and therefore favored by the present invention are deleted for all or parts of the viral E1 and E3 genes but retain as much as 80% of the adenoviral genetic material (see; e.g., Jones et al. (1979) *Cell* 16:683; Berkner et al., supra; and Graham et al. in *Methods in Molecular Biology*, E. J. Murray, Ed. (Humana, Clifton, N.J., 1991) vol. 7. pp. 109–127). Expression of the gene of interest comprised in the nucleic acid molecule can be under control of, for example, the E1A promoter, the major late promoter (MLP) and associated leader sequences, the E3 promoter, or exogenously added promoter sequences.

Yet another viral vector system useful for delivery of a nucleic acid molecule comprising a gene of interest is the adeno-associated virus (AAV). Adeno-associated virus is a naturally occurring defective virus that requires another virus, such as an adenovirus, or a herpes virus, as a helper virus for efficient replication and a productive life cycle. (For a review see Muzyczka et al. *Curr. Topics in Micro. and Immunol.* (1992) 158:97–129). Adeno-associated virusses exhibit a high frequency of stable integration (see for example Flotte et al. (1992) *Am. J. Respir. Cell. Mol. Biol.* 7:349–356; Samulski et al. (1989) *J. Virol.* 63:3822–3828; and McLaughlin et al. (1989) *J. Virol.* 62:1963–1973). Vectors containing as few as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to introduce DNA into T cells. A variety of nucleic acids have been introduced into different cell types using AAV vectors (see for example Hermonat et al. (1984) *Proc. Natl. Acad. Sci. USA* 81:6466–6470; Tratschin et al. (1985) *Mol. Cell. Biol.* 4:2072–2081; Wondisford et al. (1988) *Mol. Endocrinol.* 2:32–39; Tratschin et al. (1984) *J. Virol.* 51:611–619; and Flotte et al. (1993) *J. Biol. Chem.* 268:3781–3790). Other viral vector systems that may have application in gene therapy have been derived from herpes virus, vaccinia virus, and several RNA viruses.

In another embodiment of the invention, the nucleic acid molecule comprising a gene of interest is introduced into a T cell by non-viral-mediated methods of transfection well known in the art. These methods include electroporation, calcium phosphate precipitation, and DEAE dextran transfection.

In yet another embodiment, the nucleic acid molecule comprising a gene of interest is carried by and delivered into a T cell by a cell-delivery vehicle. Such vehicles include, for example, cationic liposomes (Lipofectin™) or derivatized (e.g. antibody conjugated) polylysine conjugates, gramicidin S, artificial viral envelopes. These vehicles can deliver a nucleic acid that is incorporated into a plasmid, vector, or viral DNA. In a specific embodiment, efficient introduction of the nucleic acid molecule in primary T lymphocytes is obtained by transfecting the primary T lymphocytes with adeno-associated virus plasmid DNA complexed to cationic liposomes, as described in Philip, R. et.al. (1994) *Mol. Cell. Biol.* 14, 2411.

In another embodiment of the invention, the nucleic acid molecule comprising a gene of interest is delivered into a specific cell in the form of a soluble molecular complex. The complex contains the nucleic acid releasably bound to a carrier comprised of a nucleic acid binding agent and a cell-specific binding agent which binds to a surface molecule of the specific T cell and is of a size that can be subsequently internalized by the cell. Such complexes are described in U.S. Pat. No. 5,166,320.

In another embodiment of the invention the nucleic acid is introduced into T cells by particle bombardment, as described in Yang, N.-S. and Sun, W. H. (1995) *Nature Medicine* 1, 481.

5. Nucleic Acid Molecules Comprising a Gene of Interest

The invention pertains to an improved method for introducing a nucleic acid molecule comprising a gene into a T cell. The language "a nucleic acid molecule" is intended to include DNA and RNA, and may be either single or double-stranded. The term "gene" is intended to include a DNA nucleotide sequence that can be transcribed into RNA or alternatively, an RNA molecule that can be translated into at least one protein.

In a specific embodiment of the invention, the gene comprises a nucleotide sequence containing one or more open reading flames, i.e., sequences that code for peptides, such that upon transfection into the T cell according to the method of the invention, at least one protein is synthesized in the T cell. The gene encoding at least one protein can be any gene, such as a gene encoding a cytokine. The gene can code for one peptide or the gene can encode several peptides.

In another embodiment of the invention, the gene is a nucleotide sequence, which upon introduction in the T cells according to the method of the invention is expressed into one or more functional RNA molecules (eg. an antisense RNA molecule). In a preferred embodiment of the invention, the functional RNA molecule inhibits, or at least decreases, expression of one or more endogenous genes in the T cell. Thus, the method of the invention is useful for decreasing expression of a selected gene in T cells. For example, T cells are transfected with a nucleic acid molecule comprising a gene encoding antisense RNA, such that translation of an endogenous RNA is reduced. An "antisense" nucleic acid comprises a nucleotide sequence which is complementary to a "sense" nucleic acid, e.g., complementary to an mRNA sequence encoding a protein, constructed according to the rules of Watson and Crick base pairing. Accordingly, an antisense nucleic acid can hydrogen bond to a sense nucleic acid. The antisense sequence complementary to a sequence of an mRNA can be complementary to a sequence found in the coding region of the mRNA or can be complementary to a 5' or 3' untranslated region of the mRNA. Preferably, an antisense nucleic acid is complementary to a region preceding or spanning the initiation codon or in the 3' untranslated region of an mRNA. For a discussion of the regulation of gene expression using antisense genes see Weintraub, H. et al., Antisense RNA as a molecular tool for genetic analysis, *Reviews—Trends in Genetics*, Vol. 1(1) 1986.

In another embodiment of the invention, expression of an endogenous gene in a T cell is reduced by introducing into the T cell a nucleic acid encoding a ribozyme according to the method of the invention. Ribozymes are catalytic RNA molecules with ribonuclease activity which are capable of cleaving a single-stranded nucleic acid, such as an mRNA, to which they have a complementary region. A ribozyme having specificity for a nucleic acid of interest can be designed based upon the nucleotide sequence of the nucleic acid. For example, a derivative of a Tetrahymena L-19 IVS RNA can be constructed in which the base sequence of the active site is complementary to the base sequence to be cleaved in an mRNA of interest. See for example Cech et al. U.S. Pat. No. 4,987,071; and Cech et al. U.S. Pat. No. 5,116,742.

The "nucleic acid molecule" comprising the gene can be a DNA molecule or an RNA molecule. The nucleic acid molecule can be a portion of a natural nucleic acid molecule, or alternatively, it can be made synthetically. The nucleic acid molecule typically contains regulatory elements to which the gene is operably linked. "Operably linked" is intended to mean that the nucleotide sequence of the gene is linked to at least one regulatory sequence in a manner which allows for expression (i.e., transcription) of the gene in T cells. Regulatory sequences are art-recognized and are selected to direct expression of the gene in an appropriate T cell. Accordingly, the term regulatory sequence includes promoters, enhancers and other expression control elements. Such regulatory sequences are known to those skilled in the art and are further described in Goeddel, *Gene Expression Technology: Methods in Enzymology* 185, Academic Press, San Diego, Calif. (1990).

These regulatory elements include those required for transcription and translation of the gene, and may include promoters enhancers, polyadenylation signals; and sequences necessary for transport of the molecule to the appropriate cellular compartment. When the nucleic acid is a cDNA in a recombinant expression vector, the regulatory functions responsible for transcription and/or translation of the cDNA are often provided by viral sequences. Examples of commonly used viral promoters include those derived from polyoma, Adenovirus 2, cytomegalovirus and Simian Virus 40, and retroviral LTRs.

Regulatory sequences linked to the cDNA can be selected to provide constitutive or inducible transcription, by, for example, use of an inducible enhancer. Thus, in a specific embodiment of the invention the nucleic acid molecule comprising a gene of interest is under the control of an inducible control element, such that expression of the gene can be turned on or off, by contacting or not contacting, respectively, the T cells containing the nucleic acid with an agent which affects the inducible control element.

In a specific embodiment, the nucleic acid molecule is under the control of an inducible control element. Inducible regulatory systems for use in mammalian cells are known in the art, for example systems in which gene expression is regulated by heavy metal ions (Mayo et al. (1982) *Cell* 29:99–108; Brinster et al. (1982) *Nature* 296:39–42; Searle et al. (1985) *Mol. Cell. Biol.* 5:1480–1489), heat shock (Nouer et al. (1991) in *Heat Shock Response*, e.d. Nouer, L., CRC, Boca Raton, Fla., pp167–220), hormones (Lee et al. (1981) *Nature* 294:228–232; Hynes et al. (1981) *Proc. Natl. Acad. Sci. USA* 78:2038–2042; Klock et al. (1987) *Nature* 3:734–736; Israel & Kaufman (1989) *Nucl. Acids Res.* 17:2589–2604 and PCT Publication No. WO 93/23431), tetracycline (Gossen, M. and Bujard, H. (1992) *Proc. Natl. Acad Sci. USA* 89:5547–5551 and PCT Publication No. WO 94/29442) or FK506 related molecules (PCT Publication No. WO94/18317).

Inducible control elements can be inducible in all T cells, or alternatively only in a specific subset of T cells, such as in $CD4^+$ T cells, $CD8^+$ T cells, T helper 1 (Th1), T helper 2 (Th2) cells. Inducible control elements could also be elements which are inducible by one agent in one type of T cells, (such as $CD4^+$ T cells) and which are inducible by another agent in another type of T cells (such as $CD8^+$ T cells).

In another embodiment of the invention, the nucleic acid molecule comprising a gene of interest is under the control of regulatory sequences which constitutively drive the expression of the nucleic acid molecule. Regulatory elements which drive constitutive expression of nucleic acid molecules to which they are operably linked can be viral elements (e.g. derived from polyoma, Adenovirus 2, cytomegalovirus, Simian Virus 40 or retrovirus). Alternatively, constitutive T cell enhancers can be used such as a T cell receptor enhancer (see e.g., Winoto and Baltimore (1989) *EMBO J.* 8:8729–733).

The nucleic acid molecule comprising a gene of interest operably linked to regulatory elements is typically carried within a vector (e.g. a plasmid or viral DNA) which includes sequences that are necessary for in vitro selection and amplification of the vector in bacteria A vector allowing for the expression of the gene carried by the vector is referred to herein as an "expression vector".

6. Applications For the Method of the Invention

The invention pertains to improved methods for introducing and expressing a gene comprised in a nucleic acid molecule into T cells. In a preferred embodiment of the invention, the T cells are primary T cells. Thus, the method of the invention allows for high level expression of a gene when introduced into primary T cells, as compared to previous methods for transfecting primary T cells. The ability to transfect primary T cells with a nucleic acid molecule comprising a gene, such that the gene is expressed in the T cells has numerous applications, in particular for gene therapy.

In one specific embodiment, peripheral blood T cells are obtained from a subject and transfected ex vivo with a nucleic acid molecule containing a gene encoding a protein of interest, such that the protein is synthesized in the T cells. The T cells may further be readministered to the subject in a specific embodiment, the exogenous protein synthesized in the T cell is secreted by the T cell. Thus, the invention provides a method for producing in an individual a secretable protein. Proteins within the scope of the invention include, for example, cytokines, lymphokines, growth factors. Thus, the proteins produced by the transfected T cell may be predominantly targeted to other cells than to T lymphocytes themselves.

Alternatively, the protein produced by the transfected T cell is an intracellular or membrane protein. In a specific embodiment, the exogenous protein is a protein that protects the T cells from an infection by, for example, a virus. Such a method is useful for expanding a population of T cells of which some are infected with a virus, such as human immunodeficiency virus (HIV). Thus, the population of T cells can be expanded without concomittant spread of the infection to all cells.

In another embodiment, the exogenous protein is a protein which kills a specific subset of T cells, such as a toxin. The protein can be selectively targeted to specific subsets of T cells by having the gene under the control of a regulatory control element specific for that subset of T cells. It is also possible to target an exogenous gene specifically to certain types of T cells by using a transfection method that allows for selective transfection of certain T cell subsets. For example, T cells can be transfected with liposomes containing on their membrane a ligand for a T cell subset specific molecule.

The gene introduced into the T cell by the method of the invention can also be a gene designed to treat a genetic disease, such as severe combined immunodeficiency due to adenine deaminase deficiency. For example, a gene encoding adenosine deaminase can be introduced into, an expressed in, primary T lymphocytes using the method of the invention. Another embodiment of the invention pertains to the treatment of hyper-IgM syndrome, a genetic disorder characterized by a mutation in the CD40 ligand (gp39) on T cells and characterized by defects in helper T cell-dependent antibody responses. Thus, T cells from a subject having hyper-IgM syndrome can be transfected ex vivo with a nucleic acid encoding gp39, preferably under the control of its own promoter, followed by administration of the T cells to the patient. Other genetic diseases resulting from a disfunctional gene in T cells, such as a gene encoding a protein involved in T cell signal transduction pathways, can be treated by the method of the invention.

The following invention is further illustrated by the following examples, which should not be construed as further limiting. The contents of all references, pending patent applications and published patents, cited throughout this application are hereby expressly incorporated by reference.

EXAMPLES

Example 1

In Vitro Long-term Culture of $CD28^+$ Peripheral Blood T Lymphocytes

Direct transfection experiments are often required to demonstrate the functional importance of putative regulatory elements in vivo. Such studies typically utilize transformed or immortalized cell lines. However, it would be preferable to study regulatory DNA sequences in the primary cells of interest. For the prospective study of cell cycle-regulated, especially $G_0$-specific, gene-expression, the maintenance of a physiological background is required. These examples were designed to develop conditions allowing for expression of exogenous DNA transfected into primary T cells.

Peripheral blood T cells were prepared as follows. Buffy coats were obtained by leukophoresis of healthy donors, aged 21 to 31 years or from the Red Cross. Peripheral blood mononuclear cells (PBMCs) were obtained by density gradient centrifugation through a Ficoll-Hypaque (Pharmacia) cushion or with Lymphocyte Separation Medium (Litton Bionetics). The $CD28^+$ subset of T cells was then isolated from the PBMCs by negative selection using immunoadsorption with goat anti-mouse Ig-coated magnetic particles (Dynal Inc.) as previously described (June, C. H., Ledbetter, J. A., Gillespie, M. M., Lindsten, T., and Thompson, C. B. (1987) *Mol. Cell. Biol.* 11:5435–5445). Cell purification was routinely monitored by flow cytometry and histochemistry. The resulting cell population was >99% $CD2^+$ and >98% $CD28^+$ as measured by fluorescence-activated cell sorter (FACS) analysis using fluorescein isothiocyanate (FITC)-conjugated mAbs. Monocytes, B cells, and large granular lymphocytes were not detectable by immunofluorescence analysis. Alternatively, resting T cells were prepared from the mononuclear cell fraction by centrifugal elutriation as previously described (Thompson, C. B., Ryan, J. J., Sieckmann, D. G., Finkelman, F. D., Mond, J. J., and Scher, I. (1983) *J. Immunol. Methods* 63:299–307). These cells were >95% $CD2^+$ as determined by flow cytometry. With both methods, cell viability was >99% as measured by trypan blue exclusion.

Human peripheral blood T cells obtained as described above were shown to be >99% $CD2^+$, >98% $CD28^+$ and in a quiescent state. The purified T cells used in this study were depleted of accessory cells and did not proliferate in vitro after stimulation with phytohemagglutinin (PHA), phorbol myristate acetate (PMA), or ionomycin alone. However, these T cells could be stimulated to divide by cross-linking the TCR-CD3 complex with immobilized monoclonal antibody (mAb) or by using appropriate amounts of PMA and ionomycin (Lindsten, T., June, C. H., and Thompson, C. B. (1988) *EMBO J.* 7:2787–2794). Under these conditions, >90% of the resting T cells were activated and the majority of the cells synchronously proceeded through one round of cell division.

To activate resting T cells and promote their long-term expansion in culture, freshly isolated resting T cells, obtained as described above, were cultured at a concentration of $2\times10^6$ cells/ml in complete medium: RPMI 1640 (GIBCO), supplemented with 10% heat-inactivated fetal calf serum (GIBCO), 2 mM L-glutamine, penicillin G (100 U/ml), streptomycin (100 mg/ml), and 15 mM Hepes (N-2-hydroxyethylpiperazine-N'-2-ethanesulfonic acid; pH 7.4; GIBCO); and rested overnight at 37° C., 5% $CO_2$. Following overnight incubation, on Day 1 of the expansion protocol, resting T cells were stimulated with a saturating quantity of immobilized anti-CD3 antibody (αCD3) mAb G19-4 directed agauist the CD3ε chain in the presence of soluble anti-CD28 antibody (αCD28) mAb 9.3 (1 μg/ml) as described by June et al., (1987) *Mol. Cell. Biol.* 11:5435–5445. CD3 mAb G19-4 (IgG1) was produced and purified as described previously (Ledbetter, J. A., Martin, P. J., Spooner, C. E., Wofsy, D., Tsu, T. T., Beatty, P. G., and Gladstone, P. (1985) *J. Immunol.* 135:2331–2336). mAb G19-4 was absorbed to the surface of plastic tissue culture flasks/plates as previously described (Geppert, T. D., and Lipsky, P. E. (1987) *J. Immunol.* 138:1660–1666) in amounts appropriate for proliferation. This was done because of the requirement for cross-linking (Williams, J. M., Ransil, B. J., Shapiro, H. M., and Strom, T. B. (1984) *J. Immunol.* 133:2986–2995) and to prevent internalization of the CD3 complex (Ledbetter, J. A., June, C. H., Martin, P. J., Spooner, C. E., Hansen, J. A., and Meier, K. E. (1986) *J. Immunol.* 136:3945–3952). CD28 mAb 9.3 (IgG2a) was purified on protein A-sepharose, dialyzed against PBS, filtered through a 0.22 μm sterile filter, cleared of aggregates by centrifugation (100,000×g for 45 min) and used at 1 μg/ml (Ledbetter, J. A., Martin, P. J., Spooner, C. E., Wofsy, D., Tsu, T. T., Beatty, P. G., and Gladstone, P. (1985) *J. Immunol.* 135:2331–2336).

Two days later, on Day 3, the activated T cells were counted, sized, and diluted to a concentration of $0.5 \times 10^6$ cells/ml with fresh complete medium. mAb 9.3 was added to a final concentration of 0.5 g/ml. Counting, sizing, and dilution of cells were repeated every 2 days until the sizing distribution shifted nearly back to a resting cell profile at which point T cells were resuspended in complete medium at $2 \times 10^6$ cells/ml and restimulated as above (first restimulation usually around Day 10).

Cells were counted using a Coulter ZM Counter (Coulter Electronics). Cells were sized on a linear scale with a Coulter Counter model ZM equipped with a cylindrical 70-μm aperture and a Channelyzer model C-256 (Coulter Electronics) interfaced to an IBM PC computer. Cells were suspended in Isoton and calibration was performed using latex beads of uniform diameters.

Treatment of mitogen or anti-T cell receptor (anti-TCR) stimulated T cells with a CD28 induced a synergistic increase in T cell proliferation. Costimulation of resting T cells with αCD3 plus αCD28 resulted in an initial period of vigorous exponential growth and cellular metabolism characterized by cellular enlargement, clumping, and acidification of the culture medium. Cells proceeded through several rounds of cell division and increased in number between 6–8 fold over the course of the first 7 to 8 days in culture. At this point, their growth rate decreased. By day 10–11 of culture, cell division ceased and cells resembled resting cells based on their size (FIG. 1). At this point in the expansion protocol, cells were restimulated with immobilized αCD3 in the presence of αCD28 and experienced another period of exponential growth characterized by cellular aggregation and enlargement.

Figure 2:
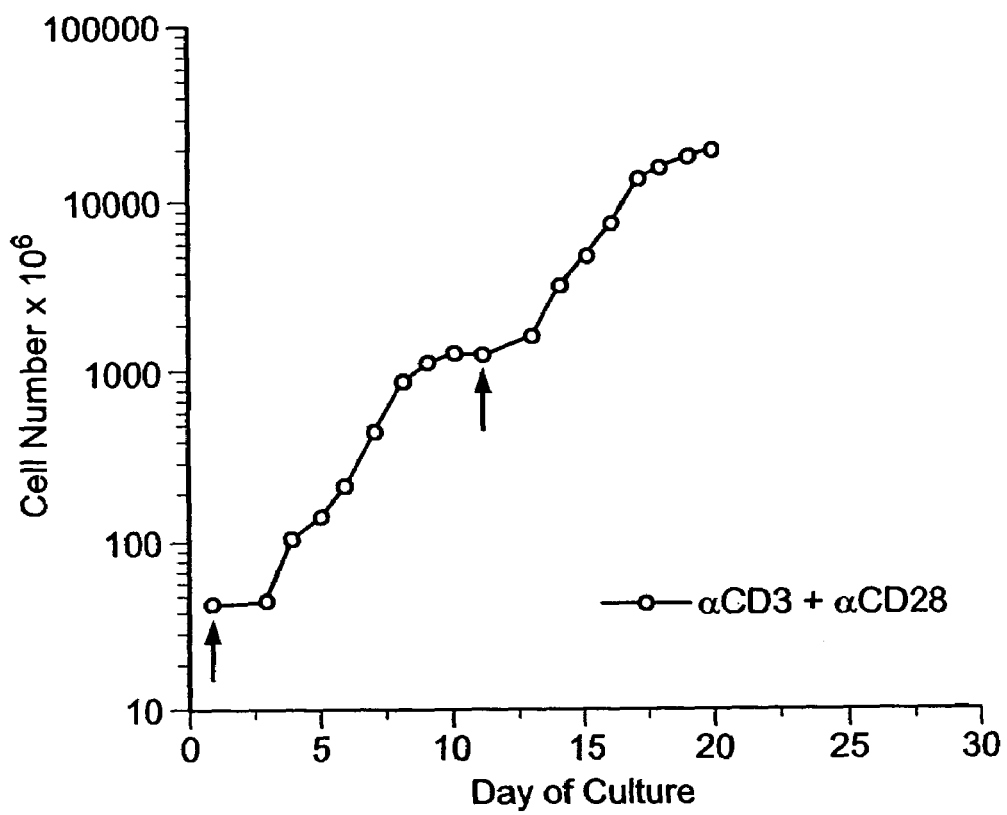
FIG. 2 represents a growth curve of freshly isolated CD28$^+$ T cells stimulated with a saturating quantity of immobilized anti-CD3 mAb G19-4 (αCD3) in the presence of the anti-CD28 mAb 9.3 (αCD28).

FIG. 2 illustrates the growth characteristics of cells cultured in this manner. As demonstrated, cells could be maintained and grown in exponential fashion for many weeks (more than 3 months) using repeated αCD3/αCD28 costimulation. Flow cytometric analysis was performed at various time points to follow the phenotypic evolution of these cells. With time, T cells expanded in this fashion became progressively more CD4$^+$45RO$^+$ reflecting a switch in phenotype from naive T helper (Th) cells to memory cells. This is in direct contrast to cells which were grown in the presence of exogenous IL-2 after αCD3/αCD28 costimulation. These cells became progressively more CD8$^+$ with time and were eventually incapable of further proliferation in culture. These observations show that some factor produced by CD4$^+$ cells is required for continuous T cell proliferation.

Example 2

Cellular Proliferation is Not Sufficient For Expression of Exogenous DNA

Having established repeated αCD3/αCD28 costimulation for the long-term clonal expansion of primary T cells, cells grown using this protocol were analyzed for endogenous ets-1 mRNA expression by Northern blot analysis.

For RNA extraction, cells were harvested by centrifugation and total cellular RNA extracted using guanidinium isothiocyanate (Chirgwin et al., 1979). The samples were equalized for rRNA, and the equalization confirmed by ethidium bromide staining of equal amounts of the RNA samples separated on a nondenaturing 1% agarose gel as described previously (June, C. H., Ledbetter, J. A., Gillespie, M. M., Lindsten, T., and Thompson, C. B. (1987) *Mol. Cell. Biol.* 11:5435–5445). These equalized RNA samples (5 to 10 μg) were separated on 1% agarose/formaldehyde gels and transferred to nitrocellulose. DNA probes were labeled by nick translation to a specific activity of 3 to $9 \times 10^8$ cpm/μg. The IL-2 specific probe was a 1.0 kb PstI cDNA insert derived from the pTCGF5 plasmid (Clark, S. C., Arya, S. K., Wong-Staal, F., Matsumoto-Kobayashi, M., Kay, R. M., Kaufman, R. J., Brown, E. L., Shoemaker, C., Copeland, T., and Oroszian, S. et al. (1984) *Proc. Natl. Acad. Sci USA* 81:2543–2547). The HLA B7 probe was a 1.4-kb PstI fragment isolated from pHLA-B7 (Sood, A. K., Pereira, D., and Weissman, S. M. (1981) *Proc. Natl. Acad. Sci. USA* 78:616–620). The ets-1 DNA probe consisted of a 442 base pair EcoRI/XbaI fragment from the 5' end of a 1.9-kb ets-1 cDNA (Ho, I-C., Bhat, N. K., Gottschalk, L. R., Lindsten, T., Thompson, C. B., Papas, T. S., and Leiden, J. M. (1990) *Science* 250:814–817). The membranes were washed and exposed to x-ray film (Kodak XAR-2 or XAR-5) for 4 hours to 7 days at −70° C. using intensifying screens.

Figure 3:
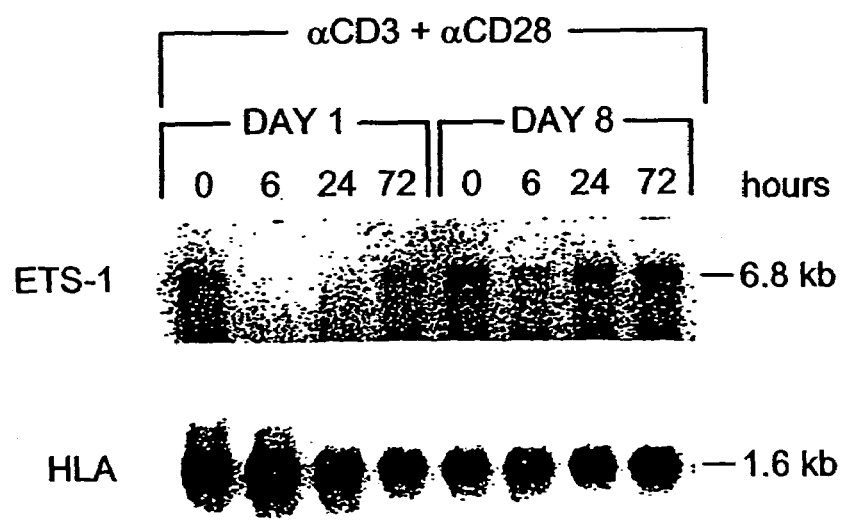
FIG. 3 is a Northern blot indicating the levels of Ets-1 (ETS-1) and human leukocyte antigen (HLA) mRNA in primary CD28$^+$ T cells cultured for 0, 6, 24, and 72 hours after the first stimulation (day 1) or a second stimulation (day 8) with a saturating quantity of immobilized anti-CD3 mAb G19-4 (αCD3) and anti-CD28 mAb 9.3 (αCD28).

For preparing Northern blots, RNA was extracted from peripheral blood T cells cultured according the protocol allowing for long term clonal expansion of primary T cells described above at various time points after activation with αCD3/αCD28 on Day 1 or after restimulation on Day 8. The results of the Northern blot analysis are presented in FIG. 3. Resting human T cells express high levels of ets-1 mRNA and protein. Resting T cells and "activated" cells on Day 8 expressed high levels of ets-1 mRNA. Upon antigen-receptor cross-linking in the presence of αCD28, ets-1 mRNA decreased to undetectable levels by 6 hours. In both cells from Day 1 and Day 8, ets-1 mRNA was expressed and maintained between 24 and 72 hours following stimulation.

To determine which cis-acting regulatory elements modulate ets-1 gene expression, primary cells in log phase growth were transfected on Day 6 of the long-term culture protocol with a plasmid containing the ets-1 promoter linked to the CAT gene (ETS-1-CAT-2). This construct exhibited robust reporter activity in Jurkat T cells. Following transfection of the primary T cell with 1 μg DNA with either DEAE-dextran (Ho, I-C., Bhat, N. K., Gottschalk, L. R, Lindsten, T., Thompson, C. B., Papas, T. S., and Leiden, J. M. (1990) *Science* 250:814–817), the cells were repeatedly washed then resuspended in complete medium 40 hours after transfection, cells were harvested and assayed for CAT activity.

With the DEAE-dextran transfection protocol, cells were washed once with PBS and then once with TS buffer pH 7.4. After the second wash, cells were resuspended at $10^7$/ml in TS buffer containing 500 µg of DEAE-dextran (molecular weight 500,000) and 1 to 10 µg of supercoiled plasmid DNA. This mixture was allowed to sit for 12 to 15 min at room temperature with occasional swirling. 10 mls of RPMI 1640 supplemented with 20% heat-inactivated fetal calf serum, 2 mM L-glutamine, and 15 mM Hepes (RPMI 1640/20% FCS/G/H was added to the cells. The cells were transferred to tissue culture flasks and incubated for 30 min at 37° C., 5% $CO_2$. The cells were then pelleted, washed once with RPMI 1640/20% FCS/G/H, and resuspended in 10 ml RPMI 1640/20% FCS/G/H at 37° C., 5% $CO_2$.

In other examples described herein, primary T cells are transfected by electroporation. With the electroporation protocol, cells were washed twice with ice-cold PBS and resuspended at $20 \times 10^6$ cells/ml in ice-cold RPMI 1640/20% FCS/G/H. $6 \times 10^6$ cells in 300 µl were transferred to a sterile 0.4 cm electroporation cuvette (BioRad). 1 to 10 µg of reporter plasmid was added and the cells electroporated using a gene pulser (BioRad) at 250 V and 960 µfarads. The cells were incubated 10 min on ice, diluted to 10 ml with RPMI 1640/20% FCS/GIH and placed at 37° C., 5% $CO_2$.

Equal volumes of cell extracts were assayed for CAT activity in a 16 hour reaction. EDTA was added to a final concentration of 5 mM and the extracts heated at 65° C. for 10 min to prevent the hydrolysis of acetyl-CoA and the deacetylation of chlorainphenicol (Crabb, D. W., and Dixon, J. E. (1987) *Anal. Biochem.* 163:88–92). Before autoradiography of the CAT assay thin-layer chromatography (TLC) plate, spots corresponding to [$^{14}$C]chloramphenicol and its acetylated derivatives were quantitated using a Betascope (Betagen) or phosphorimager (Molecular Dynamics). The percent acetylation was calculated after subtracting background values from experimental acetylated and non-acetylated values. If the percent acetylation was out of the linear range of the assay for a given set of transfections, equal volumes of cell extracts were diluted, and the CAT assay reperformed. CAT activity was then normalized to the amount of protein in the reaction. Normalized CAT activity is expressed as percent acetylation/mg protein)×50. All comparisons of reporter activity derive from cells stimulated, transfected, harvested, and assayed at the same time with the same reagents.

No ETS-1-CAT-2 reporter activity was detected in primary cells transfected in this manner. Since endogenous ets-1 mRNA is preferentially expressed in resting cells and is reinduced approximately 2–3 days following T cell stimulation, ETS-1-CAT-2 reporter expression was expected, whether or not T cells reentered a resting state. Surprisingly, transfection of cells with positive controls such as RSV-CAT, HIV-1-CAT, and HTLV-1-CAT, also yielded no demonstrable reporter activity. Based on increases in cell number, cells at Day 6 of the long-term culture protocol were in log-phase growth (FIG. 2). However, transfection of these cells with constitutive reporter constructs resulted in no detectable reporter activity suggesting that proliferation alone is insufficient for efficient transgene expression.

To determine whether "active" signal transduction is required for reporter gene expression, primary T cells in log phase growth on Day 5 of the culture protocol were stimulated with phorbol ester (PDBU) plus calcium ionophore (ionomycin) 10 hours before transfection.

Figure 4:
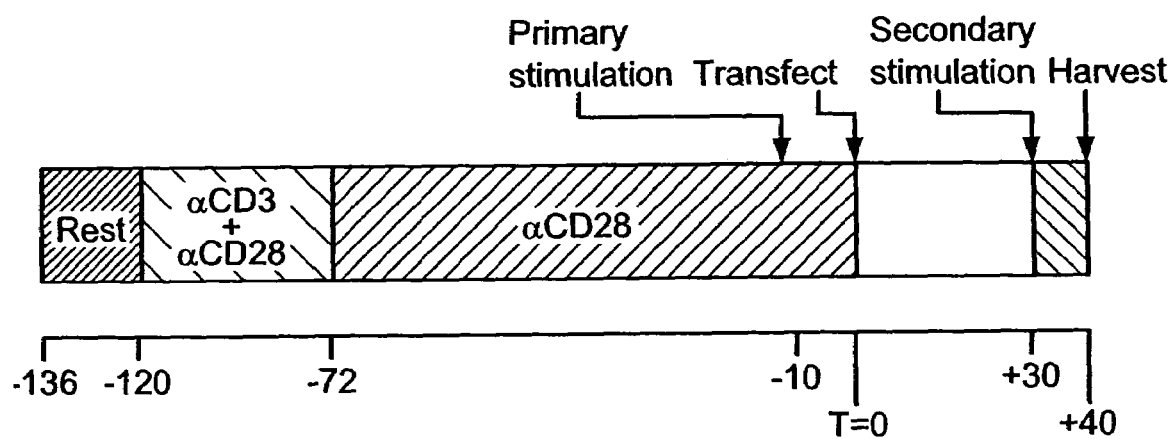
FIG. 4 is a schematic representation of an example of a transfection protocol in which resting T cells (Rest) are first incubated with anti-CD3 and anti-CD28 (αCD3+αCD28) for two days, followed by incubation with anti-CD28 alone (αCD28) for 3 days, stimulated (primary stimulation) 10 hours prior to transfection, transfected at T=0, restimulated (secondary stimulation) at 30 hours post transfection, and harvested 10 hours later.

FIG. 4 depicts the timetable used for this and subsequent transfections. Resting T cells were stimulated to proliferate by incubation with a saturating amount of immobilized anti-CD3 antibody-and anti-CD28 at 1 µg/ml. Two days later, on Day 3, the activated T cells were counted, sized, and diluted to a concentration of $0.5 \times 10^6$ cells/ml with fresh complete medium. mAb 9.3 was added to a final concentration of 0.5 µg/ml. At day 5, cells were stimulated with-phorbol-12,13-dibutyrate (PDBU; from LC Services Corp.) at 10 ng/ml and ionomycin (Calbiochem) at 0.4 µg/ml. On Day 6, 10 hours after stimulation, cells were transfected with 10 µg of constitutively expressed reporter construct RSV-CAT using DEAE-dextran essentially as previously described (Ho, I-C., Bhat, N. K, Gottschalk, L. R., Lindsten, T., Thompson, C. B., Papas, T. S., and Leiden, J. M. (1990) *Science* 250:814–817). pRSV-CAT (RSV-CAT) consists of RSV-LTR sequences fused to the 5' end of coding sequences for CAT (Gorman, C. M., Merlino, G. T., Willingham, M. C., Pastan, I., and Howard, B. H. (1982) *Proc. Natl. Acad. Sci. USA* 79:6777–6781). Cells were harvested 40 hours later and assayed for CAT activity.

Figure 5:
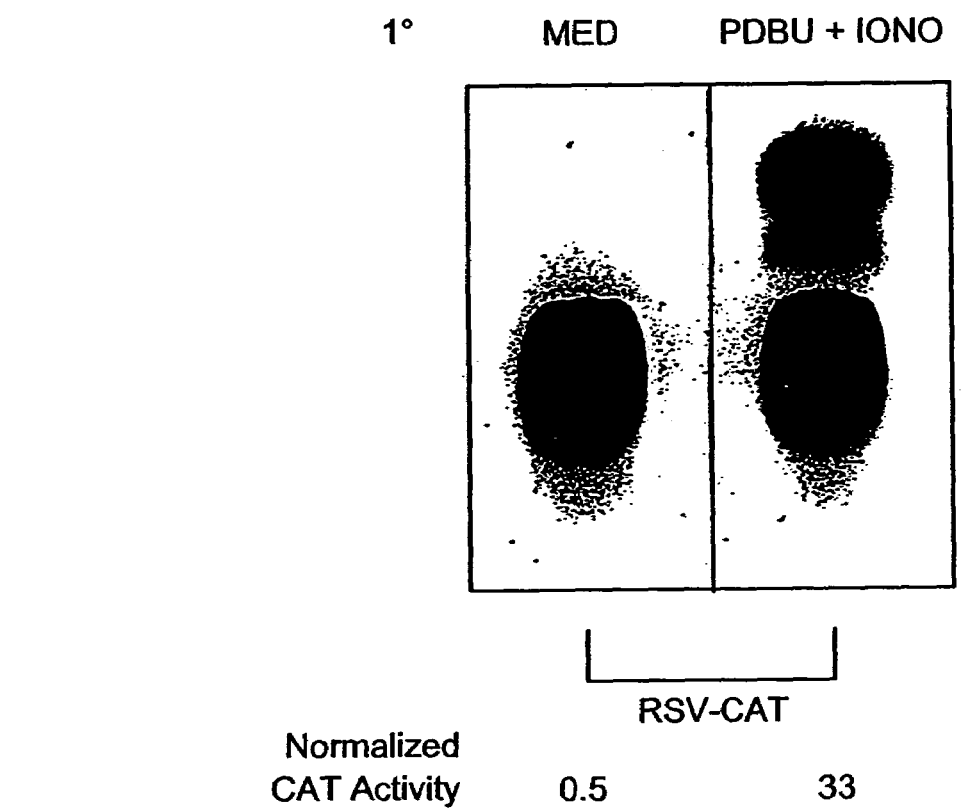
FIG. 5 represents the results of CAT assays performed with cell extracts from exponentially growing T cells transfected with RSV-CAT stimulated 10 hours before transfection with phorbol-12,13-dibutyrate and ionomycin (PDBU+ IONO) or conditioned medium alone (MED) and harvested 40 hours post transfection. Normalized CAT activity is expressed as (% acetylation/mg protein)×50.

The results are presented in FIG. 5. PDBU+ionomycin prestimulation of proliferating primary cells resulted in a 67-fold increase in RSV-CAT reporter expression relative to cells treated with conditioned medium alone. To determine whether this dramatic difference in RSV-CAT reporter activity was due to a difference in the proliferative capacity of stimulated versus non-stimulated cells, the proliferative status of these cells was measured using the following: 1) acridine orange staining for cell cycle analysis; 2) tritiated thymidine [$^3$H]TdR incorporation as a measure of DNA synthesis; and 3) cell sizing as a general measure of cellular activation. Autologous resting primary cells and αCD3/αCD28 stimulated cells from Day 3 of the long-term culture protocol were measured simultaneously as controls for the quiescent state ($G_0/G_1$ interface) and robust proliferation.

Purified resting T cells (Day 1) were stimulated with a saturating quantity of immobilized αCD3 mAb G19-4 in the presence of the αCD28 mAb 9.3 (1 µg/ml). On Day 3, activated T cells were diluted to a concentration of $0.5 \times 10^6$/ml with fresh complete medium and mAb 9.3 added to a final concentration of 0.5 µg/ml. On Day 6, T cells in exponential growth were treated with phorbol-12,13-dibutyrate (PDBU) (10 ng/ml) plus ionomycin (0.4 µg/ml) or conditioned medium alone for 10 hr. Cells from Day 3 and Day 6 were stained with acridine orange for cell cycle analysis as described below. Unstimulated cells (Day 1) were analyzed simultaneously to determine the $G_0/G_1$ interface.

Cells were analyzed for DNA and RNA content on a FACScan flow cytometer (Becton-Dickinson) after staining with acridine orange (Polysciences) using a procedure described by Darzynkiewicz (1990) *Methods Cell Biol*, 33:285–298) 1 to $5 \times 10^6$ cells were washed two times with PBS and fixed in cold 70% ethanol at a concentration of $2 \times 10^6$/ml. Cells were centrifuged, washed, and resuspended in complete medium at a concentration below $2 \times 10^6$/ml. 0.2 ml of this cell suspension was stained with acridine orange, and analyzed on the FACScan. Cells with increased RNA content and unchanged DNA content were considered $G_1$ phase cells. Cells with increased RNA and DNA content were considered in S or $G_2M$ phases.

For determining [$^3$H]TdR incorporation of T cells from Days 1, 3, and 6, cells were cultured in quadruplicate samples in flat-bottom 96-well microtiter plates (Costar) at $5 \times 10^5$ cells/well. The final culture volume was 200 µl in complete medium. 1 µCi of tritiated thymidine [$^3$H]TdR (ICN) was added to each well and the cultures incubated for 6 hours at 37° C., 5% $CO_2$. After 6 hours of culture the cells were harvested onto glass microfiber strips (Whatman) using a PHD cell harvester (Cambridge Technologies) and counted in a liquid scintillation counter (LKB). All values are expressed as the mean cpm±standard deviation of quadruplicate cultures.

Figures 6A, 6B, 6C, 6D:
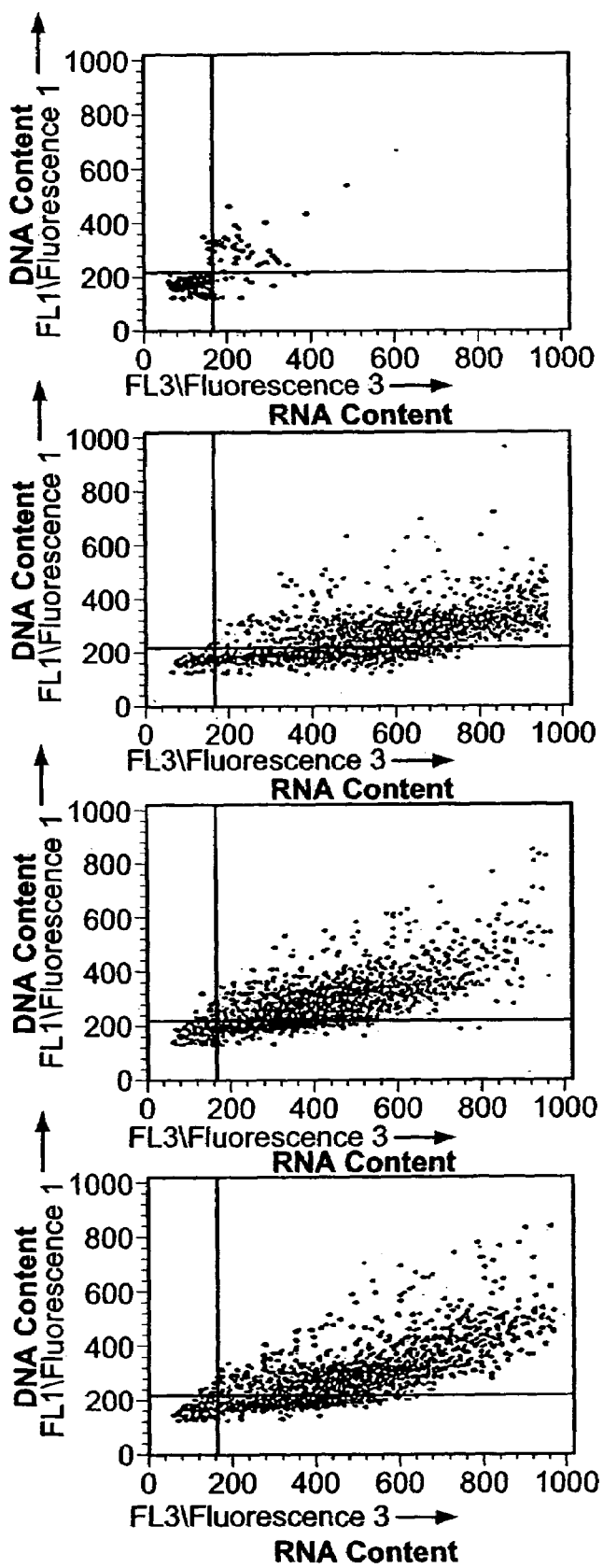
FIG. 6 (Panels A–D) depicts the results of flow cytometric analysis of acridine orange stained primary T cells and proliferation assays of primary T cells cultured under the following conditions: untreated resting primary T cells (Panel A), T cells stimulated for 3 days with anti-CD3 and anti-CD28 (Panel B), T cells stimulated for 3 days with anti-CD3 and anti-CD28 and then incubated in fresh medium for another 3 days (Panel C), or T cells stimulated for 3 days with anti-CD3 and anti-CD28, stimulated for 10 hours with phorbol-12,13-dibutyrate (PDBU) plus ionomycin and then incubated in fresh medium for another 2 days and 14 hours (panel D). The graphic representations of flow cytometric analysis of acridine orange stained cells indicate the DNA and RNA content of the cells, which is indicative of the number of cells in Go (% Go), G1 (% G1), and S/G2M (% S/G2M) phase of the cell cycle.

As shown in FIG. 6, stimulation of resting T cells with αCD3/αCD28 resulted in progression of greater than 92% of the cells from $G_0$ to $G_1$ or $S/G_2M$ phases of the cell cycle by the third day of cellular expansion. This corresponded to a 207-fold increase in tritiated thymidine incorporation and an increase in mean cellular volume. By Day 6 of culture, greater than 91% of cells growing in conditioned medium alone were in either $G_1$ or $S/G_2M$ phases of the cell cycle. Greater than 92% of PDBU+ionomycin treated cells assayed for RNA and DNA content 10 hours after stimulation were found to be in $G_1$ or $S/G_2M$ phases of the cell cycle. These data illustrate the actively cycling nature of cells at the time of transfection and the equivalent proliferative capacities of PDBU/IONO stimulated versus non-stimulated cells. Indeed, PDBU/IONO stimulated cells did not demonstrate any increase in the rate of DNA synthesis ($35 \times 10^3$ cpm versus $52 \times 10^3$ cpm [$^3$H]TdR incorporation) or mean cellular volume when compared to their non-stimulated counterparts. Thus, no differences in the proliferative capacities of these two cell populations were found at the time of transfection which would account for differences in RSV-CAT reporter gene expression.

Figure 7:
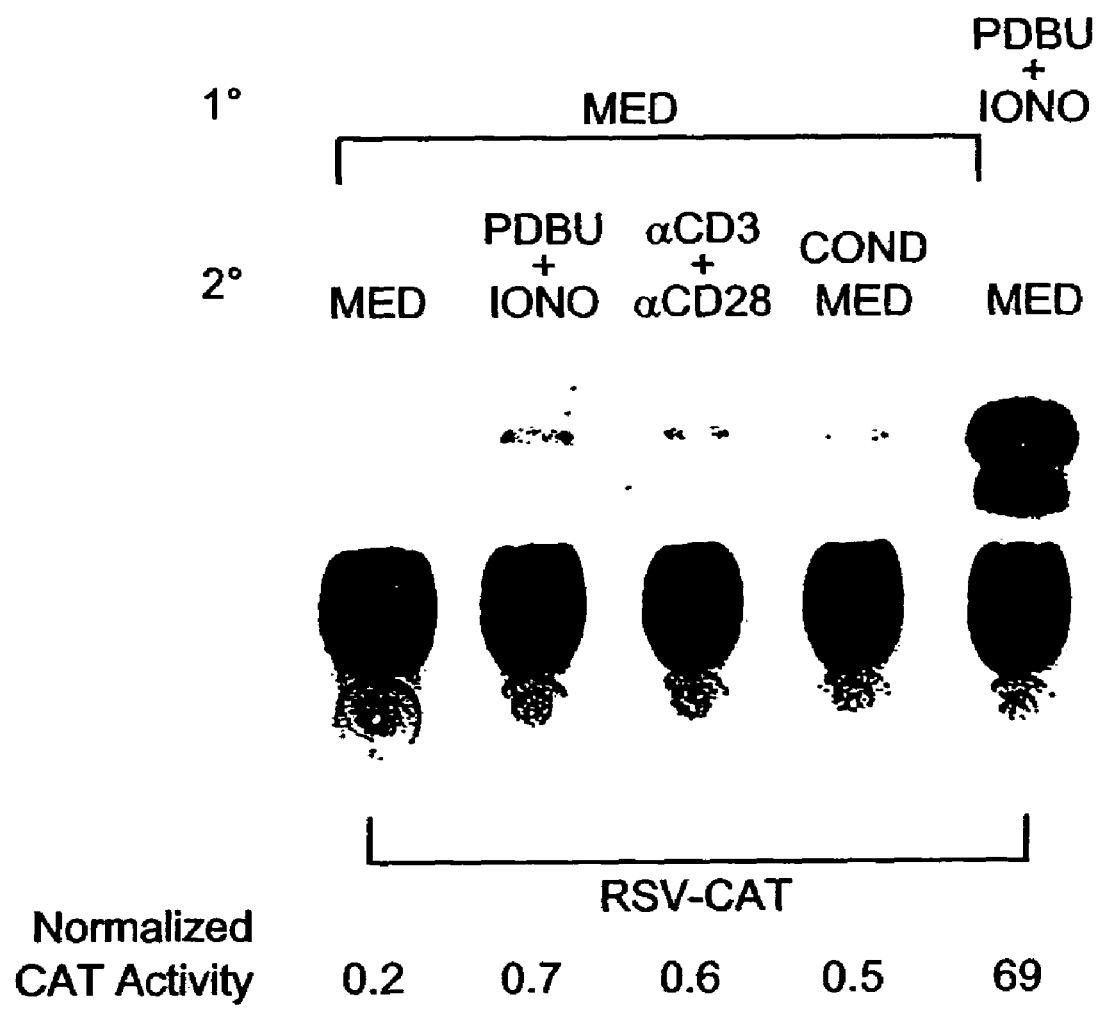
FIG. 7 represents the results of CAT assays performed with cell extracts from exponentially growing T cells transfected with RSV-CAT and stimulated 10 hours before transfection (1°) with medium alone (MED) or phorbol-12,13- dibutyrate and ionomycin (PDBU+IONO) and stimulated 30 hours after transfection (2°) with medium alone (MED), phorbol-12,13-dibutyrate and ionomycin (PDBU+IONO), anti-CD3 and anti-CD28 antibodies (αCD3+αCD28), or conditioned medium (COND MED) and harvested 10 hours later. Normalized CAT activity is expressed as (% acetylation/mg protein)×50.

The Rous sarcoma virus LTR contains a calcium/calmodulin-dependent protein kinase (CaM-kinase) response element which is capable of conferring selective induction of transcription by activated CaM-kinase in the presence of elevated levels of calcium ions (Kapiloff, M. S., Mathis, J. M., Nelson, C. A., Lin, C. R., and Rosenfeld, M. G. (1991) *Proc. Natl. Acad. Sci. USA* 88:3710–3714). To determine whether differences in RSV-CAT expression between PDBU/IONO stimulated and non-stimulated cells arose from specific trans-activation of the RSV LTR following stimulation, cells were either prestimulated with PDBU/IONO or treated with conditioned medium alone, transfected, then either immediately cultured in conditioned medium or complete medium. 30 hours after transfection, cells cultured in complete medium were either stimulated with PDBU/IONO, αCD3/αCD28, or were treated with medium alone. 10 hours later, cells were harvested for CAT activity. If the only role of signal transduction is to activate transcription off the RSV LR, then cells stimulated after transfection should also demonstrate increased reporter activity. As shown in FIG. 7, PDBU/IONO prestimulation of cells resulted in a 345 fold increase in RSV-CAT reporter activity-relative to the non-stimulated proliferating control. Stimulation of cells 30 hours after transfection with either αCD3/αCD28 or PDBU/IONO resulted in a small 3- or 3.5-fold increase in RSV-CAT reporter activity, respectively. Culturing of transfected cells in growth-competent conditioned medium resulted in a 2.5-fold increase in CAT activity. In addition, PDBU/IONO or αCD3/αCD28 stimulation of cells immediately after transfection resulted in a small 4 to 5-fold increase in RSV-CAT activity. These data demonstrate that stimulation before transfection is required for RSV-CAT activity and suggest signal transduction at the time of transfection facilitates reporter gene expression either by increasing transfection efficiency or by rendering the transgene competent for expression. Using this reporter construct, stimulation of cells post-transfection did not result in an appreciable increase in reporter gene expression.

Figure 8:
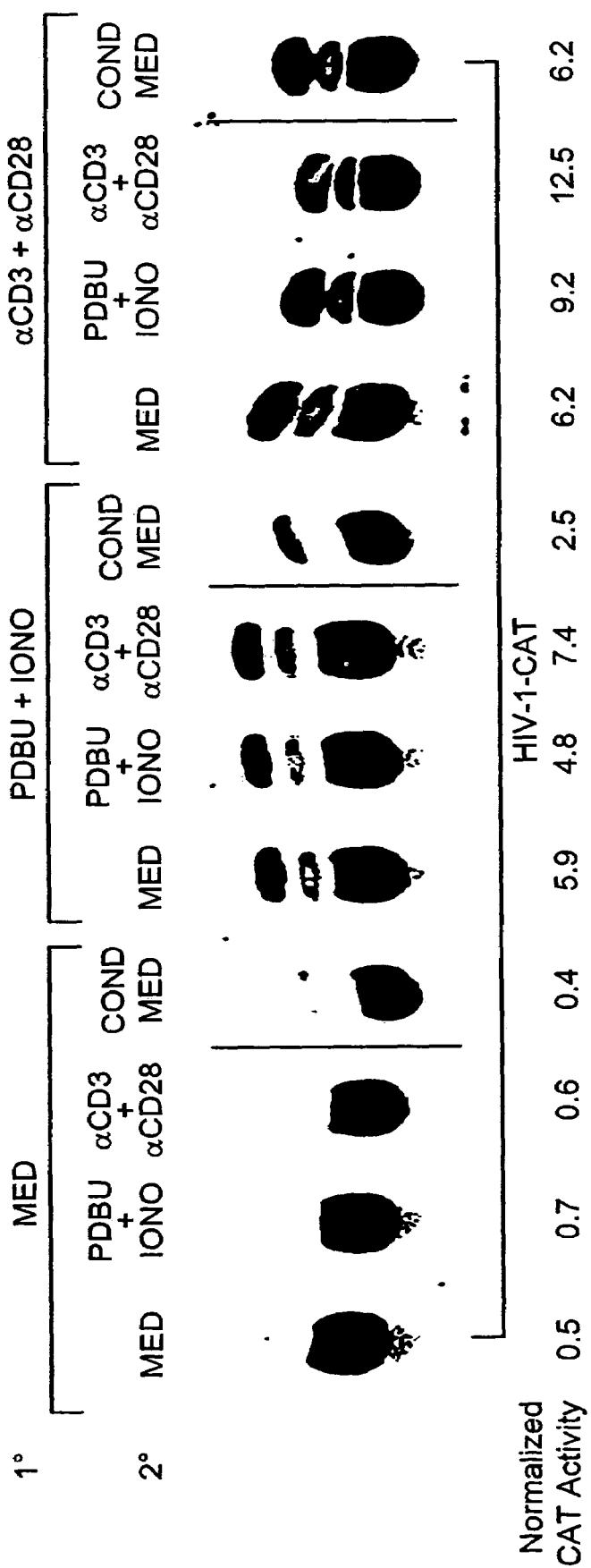
FIG. 8 represents the results of CAT assays performed with cell extracts from exponentially growing T cells transfected with an HIV-1-CAT expression construct and stimulated 10 hours before transfection (1°) with media alone (MED), phorbol-12,13-dibutyrate and ionomycin (PDBU+IONO), or anti-CD3 and anti-CD28 antibodies (αCD3+αCD28) and stimulated 30 hours after transfection (2°) with media alone (MED), phorbol-12,13-dibutyrate and ionomycin (PDBU+IONO), anti CD3 and anti-CD28 antibodies (αCD3+αCD28), or conditioned medium (COND MED) and harvested 10 hours later. Normalized CAT activity is expressed as (% acetylation/mg protein)×50.

In the following example, it was shown that stimulation of primary T cells with anti-CD3 and anti-CD28 10 hours prior to transfection also resulted in greatly enhanced expression of the reporter construct. HIV-1-CAT has been described previously (Nabel, G., and Baltimore, D. (1987) *Nature* 326:711–713), was used in this example. Proliferating T cells were prestimulated with either PDBU/IONO, αCD3/αCD28, or treated with conditioned medium alone, transfected with HIV-1-CAT, then either immediately cultured in conditioned medium or stimulated 30 hours after transfection with PDBU/IONO, αCD3/αCD28, or medium alone. 10 hours later, the cells were harvested and assayed for CAT activity. Results of the CAT assays are shown in FIG. 8. The results indicate that prestimulation of primary T cells 10 hours prior to transfection greatly enhances expression of the HIV-1-CAT reporter contact compared to transfection without prestimulation. Thus, the enhancement of expression of the reporter construct is not dependent on the type of promoter and enhancer in the construct. Moreover, these results indicate that prestimulation of the primary T cells to enhance expression of the transfected reporter construct can also be done with a combination of anti-CD3 and anti-CD28 antibodies.

Example 3

Expression of Exogenous DNA Requires TCR-dependent Signal Transduction at the Time of Transfection To further dissect the requirements for efficient transgene expression in primary T cells, the extensively studied and well characterized promoter/enhancer of the cellular IL-2 gene was used in transfection experiments. Northern blot analysis was used to characterize the kinetics of IL-2 gene expression after stimulation of the TCR-CD3 complex by optimal amounts of immobilized αCD3. In addition, the supernatants from these cultures were also analyzed for IL-2 content and the cells analyzed for cell cycle progression.

Figure 9:
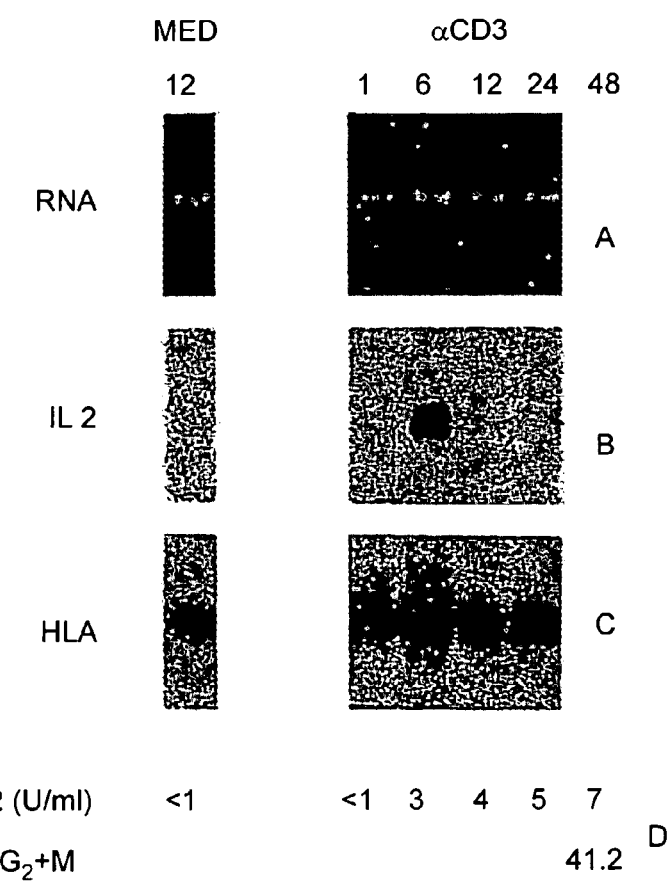
FIG. 9 represents total RNA content (Panel A) or levels of mRNA for IL-2 (Panel B) and HLA (Panel C) determined by Northern blot analysis in $CD28^+$ T cells cultured with medium alone (MED) for 12 hours or with anti-CD3 antibody (CD3) for 1, 6, 12, and 24 hours. Panel D indicates the amount of IL-2 produced by the T cells incubated with medium alone (MED) for 12 hours or with anti-CD3 antibody (CD3) for 1, 6, 12, 24, or 48 hours and the percentage of the cells in phase S, G2 or M of the cell cycle after 48 hours of culture with anti-CD3.

The results are presented in FIG. 9. Panel B indicates that in the presence of optimal αCD3 stimulation, IL-2 mRNA expression peaked at 6 hours of culture by 12 hours of culture IL-2 mRNA levels had decreased to undetectable levels. This transient induction of IL-2 mRNA expression was accompanied by a small amount of IL-2 in the culture supernatant (5 U/ml at 24 hours) and vigorous proliferation (41% of cells in $S/G_2M$ phases of the cell cycle by 48 hours) (Panel D). To summarize, stimulation of the TCR-CD3 complex resulted in the transient induction of IL-2 gene transcription peaking 6 hours and decreasing to undetectable levels by 12 hours post-stimulation.

Given the inducible and transient nature of IL-2 mRNA transcription, the requirement of signal transduction at the time of transfection for IL2-CAT reporter gene expression was tested. The pIL2CAT plasmid (IL2-CAT) contains the IL-2 promoter/enhancer (−585 to +18) immediately 5' of the chloramphenicol acetyltransferase (CAT) gene and has been described previously (Bielinska, A., Shivdasani, R. A., Zhang, L., and Nabel, G. J. (1990) *Science* 250:997–1000). Proliferating primary T cells on Day 5 of the expansion protocol were either prestimulated with PDBU/IONO or treated with conditioned medium alone, transfected with the IL2-CAT reporter plasmid, then immediately cultured in growth competent conditioned medium or complete medium. 30 hours after transfection, cells cultured in complete medium were stimulated with either PDBU/IONO, αCD3/αCD28, or were treated with medium alone. 10 hours later, cell number and viability were determined by trypan blue exclusion, and cells harvested for CAT activity.

Figure 10:
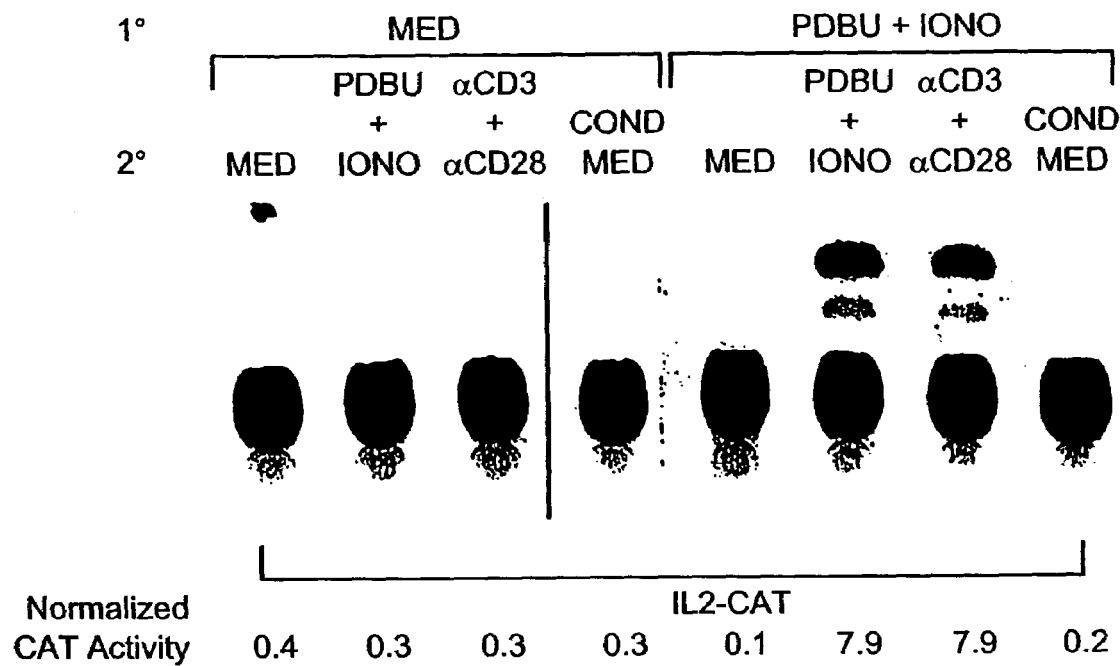
FIG. 10 represents the results of CAT assays performed with cell extracts from exponentially growing T cells transfected with an IL2-CAT expression construct and stimulated 10 hours before transfection (1°) with media alone (MED) or phorbol-12,13-dibutyrate and ionomycin (PDBU+IONO) and stimulated 30 hours after transfection (2°) with media alone (MED), phorbol-12,13-dibutyrate and ionomycin (PDBU+IONO), anti-CD3 and anti-CD28 antibodies (αCD3+αCD28), or conditioned medium (COND MED) and harvested 10 hours post-transfection. Normalized CAT activity is expressed as (% acetylation/mg protein)×50.

The CAT assay results are shown in FIG. 10 and are summarized as follows: 1) In the absence of prestimulation, proliferating primary cells expressed extremely low levels of IL2-CAT reporter, 2) Stimulation of cells 30 hours after transfection did not increase this low level of IL2-CAT reporter gene expression; 3) Following PDBU/IONO prestimulation and transfection, cells resuspended in lymphokine rich conditioned medium or complete medium also expressed extremely low levels of IL2-CAT reporter; 4) However, following both PDBU/IONO prestimulation and TCR-directed stimulation 30 hours after transfection, IL2-CAT reporter activity increased 79-fold relative to cells which only received prestimulation and approximately 20-fold relative to the non-stimulated proliferating control. Therefore, IL2-CAT reporter gene expression required TCR-dependent signal transduction both before and after transfection. These data are consistent with a model in which the introduction of the IL2-CAT DNA reporter construct into an expressible compartment or state requires TCR-dependent signal transduction before transfection. However, even though the IL2-CAT reporter plasmid is competent for expression, little or no IL2-CAT transcription occurs since the initial signal transduction was delivered 10 hours before transfection and by the above Northern analysis (FIG. 9), IL-2 mRNA transcription decreases to low levels by this timepoint. TCR/CD3-dependent stimulation after transfection results in trans-activation of the expression-competent IL-2 promoter enhancer and CAT mRNA transcription with resulting reporter activity.

Example 4

Cellular Proliferation is Required For Transgene Expression

Figure 11:
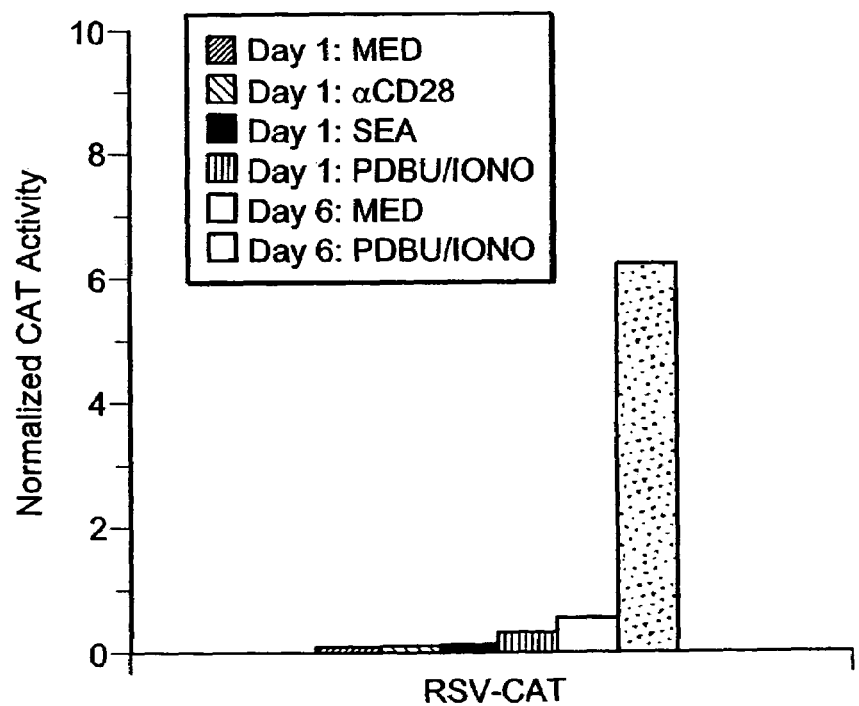
FIG. 11 represents the results of CAT assays performed with cell extracts from resting T cells transfected with RSV-CAT and treated 10 hours before transfection with medium alone (Day1: MED), anti-CD28 (Day 1: αCD28), Staphylococcal enterotoxin A (Day 1: SEA), or phorbol-12,13-dibutyrate and ionomycin (Day 1: PDBU+IONO), or with anti-CD3 and anti-CD28 for 5 days and then for 10 hours before transfection with conditioned medium (Day 6: MED) or phorbol-12,13-dibutyrate and ionomycin (Day 6: PDBU+IONO). Normalized CAT activity is expressed as (% acetylation/mg protein)×50.

To address the role of cellular proliferation in transgene expression, freshly isolated resting T cells were stimulated with either αCD28 (1 g/ml), SEA (10 ng/ml, Toxin Technologies), PDBU (10 ng/ml)/IONO (0.4 µg/ml), or medium alone for 10 hours. These cells were transfected with RSV-CAT, then harvested 40 hours later for CAT activity. Activated T cells undergo cell division between 24–36 hours after mitogenic stimulation. Therefore, at the time of transfection, very few, if any, T cells have progressed through M phase. By 40 hours post-transfection (approximately 50 hours post-stimulation), T cells stimulated with SEA or PDBU/IONO did exhibit phenotypic changes associated with proliferation (cellular enlargement, aggregation). However, these populations had not increased in cell number. As shown in FIG. 11, the normalized CAT activities for all these transfection conditions were relatively low (0.07–0.26). Resting cells stimulated with PDBU/IONO demonstrated a small 3.7-fold increase in RSV-CAT activity relative to the resting control. This small increase in CAT activity between PDBU/IONO stimulated and resting cells may simply reflect the effects of cellular activation and proliferation on RSV LTR transcription once this reporter plasmid is capable of expression as a result of the initial signal transduction. Of note, the CAT activities of cells stimulated with αCD28 or SEA were no different from that of resting cells. Neither αCD28 nor SEA alone constitute complete mitogenic stimuli. The induction of T-cell proliferation by SEA requires the addition of a second costimulatory signal provided by accessory cells (a requirement for major histocompatibility complex (MHC) Class II presentation) or of monoclonal antibody stimulation of CD28 (Green, J. M., Turka, L. A., June, C. H., and Thompson, C. B. (1992) *Cell. Immunol.* 145(1):11–20). Resting T cells do not express MHC Class II (HLA-Dr) on their surface (Mayforth, R. D.(1991) Ph. D. Dissertation, Univ. of Chicago). Thus, in the absence of proliferative stimuli, resting T cells do not demonstrate expression of the constitutively active reporter plasmid RSV-CAT.

To demonstrate that these cells could express RSV-CAT, another aliquot of the same cells was stimulated with αCD3/αCD28 and passaged in culture. 5 days later, these cells were either stimulated with PDBU/IONO or were treated with conditioned medium alone for 10 hours, transfected with RSV-CAT, then harvested 40 hours later for CAT activity. A comparison of the relative CAT activities of cells transfected either on Day 1 (resting cells) or Day 6 (proliferating cells) in the presence or absence of PDBU/IONO prestimulation is shown in FIG. 11. PDBU/IONO prestimulation of proliferating cells resulted in a 13.4-fold increase in CAT activity relative to the proliferating non-stimulated control and a 23.7-fold increase over PDBU/IONO stimulated resting cells. Thus, cellular proliferation at the time of transfection greatly enhances RSV-CAT reporter expression. Taken together with the results of the transfections above, these data indicate that proliferation is required but not sufficient for transgene expression.

Example 5

Differences in Reporter Gene Activity Are Not Due to Differences in Transfection Efficiency As demonstrated above, TCR-dependent signal transduction prior to the time of transfection is required for transgene expression. Stimulation after transfection does not appreciably increase reporter activity in most cases. The critical factor is the activational state of the cell, independent of proliferation, at the time of transfection. Any of a number of roles for signal transduction can be envisioned. In the simplest model signal transduction off proliferating cells at the time of transfection could increase transfection efficiency and therefore the amount of reporter plasmid reaching the nucleus. Alternatively, signal transduction could facilitate the movement of transfected DNA from a non-transcribable to transcribable compartment, e.g., from the cytoplasm to nucleus. Both scenarios result in equivalent outcomes, an increased amount of reporter plasmid in the nucleus following signal transduction. To test these possibilities, the kinetics of DNA entry and localization were examined by rescuing and quantitating transfected DNA from nuclear and cytoplasmic compartments at various timepoints after transfection.

Proliferating primary T cells on Day 5 were prestimulated with PDBU/IONO or treated with conditioned medium alone, transfected with the RSV-CAT reporter plasmid, then cultured in complete medium. At 0, 6, 24, and 48 hours after transfection, cell number and viability were determined by Coulter counting and trypan blue exclusion respectively.

Following separation into nuclear and cytoplasmic fractions by Dounce homogenization, DNA was extracted from both these fractions using serial ammonium acetate/isopropanol precipitations following SDS solubilization and Proteinase K digestion. The DNA isolation protocol is quantitative for the recovery of both low and high molecular weight DNA. To estimate the relative copy numbers of the transgene in nuclear and cytoplasmic compartments at various timepoints after transfection, nuclear and cytoplasmic DNA from $10^5$ total cell equivalents was size-fractionated in 1.0% agarose gels and transferred onto nitrocellulose as previously described (Thompson, C. B., and Neiman, P. E. (1987) *Cell* 48:369–378). Blots were hybridized with either an EcoRI fragment from the CAT coding region of pRSV-CAT or an EcoRI/BamHI fragment from the CAT coding region of pIL2CAT.

Figure 12A:
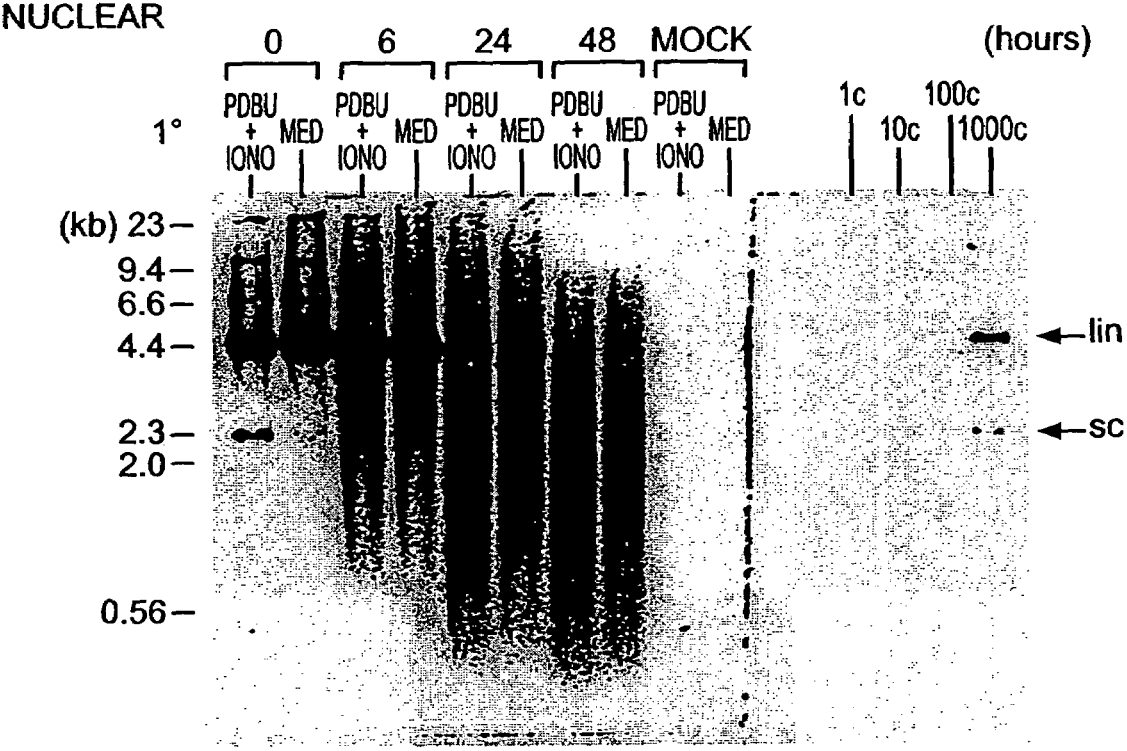
FIG. 12 shows autoradiograms of Southern blots of nuclear DNA (NUCLEAR, Panel A) or cytoplasmic DNA (CYTO, Panel B) extracted from proliferating T cells 0, 6, 24, or 48 hours after transfection of the proliferating T cells with RSV-CAT or no plasmid (MOCK), stimulated 10 hours prior to the transfection with phorbol-12,13-dibutyrate and ionomycin (PDBU+IONO) or conditioned medium alone (MED) and hybridized with an EcoRI fragment from the CAT coding region of RSV-CAT. Plasmid DNA corresponding to 1 (1c), 10 (10c), 100 (100c), and 1000 (1000c) copies of RSV-CAT/ell was used as a control. (lin) linear plasmid; (sc) supercoiled plasmid. The size of fragments (in kilobases, kb) from a molecular weight marker is represented on the left of the Southern blots.
Figure 12B:
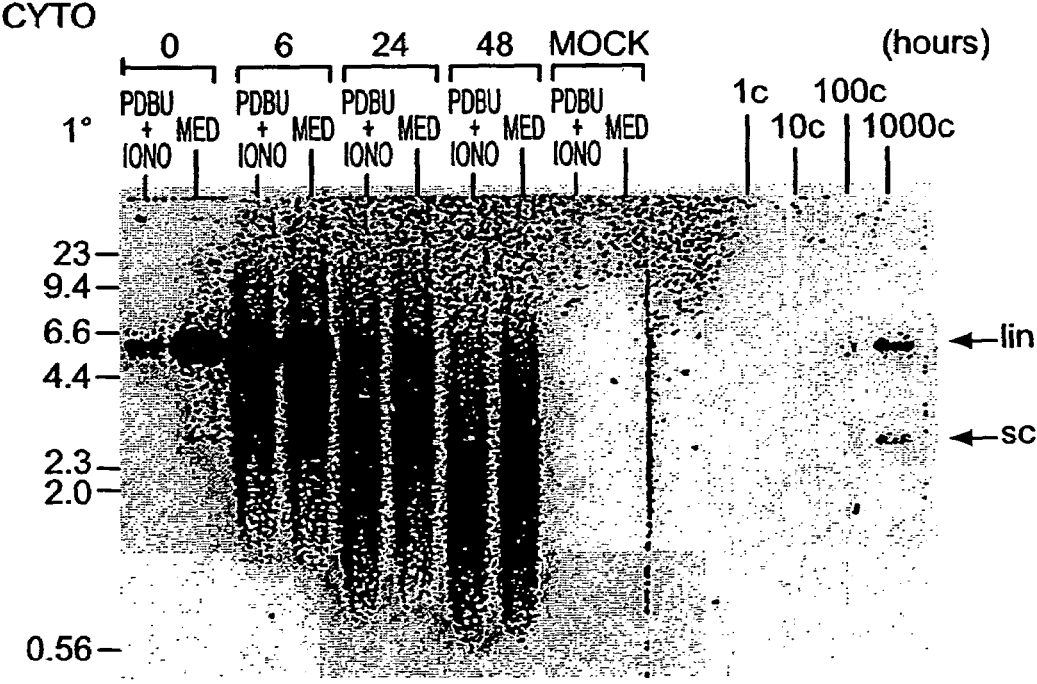

The results of the Southern blot analysis are presented in FIG. 12. Approximately $10^5$ copies of plasmid/cell were taken up within the first 30 minutes of exposure to DNA/DEAE dextran complexes. This corresponds to approximately 10% of the total DNA transfected. Of this amount, approximately 90% localized to the nuclear fraction. Similar, or slightly increased, levels of transgene were present in the nuclear and cytoplasmic fractions of cells at 6, 24, and 48 hours after transfection. Significantly, there was no appreciable difference in the amount of DNA in either nuclear or cytoplasmic fractions between PDBU/IONO prestimulated and non-stimulated cells at any of the timepoints. In sum, Southern analysis revealed no demonstrable difference in the amount of DNA reaching the nuclear compartment between signal transduced and non-signal transduced cells.

To confirm these findings, primary T cells were transfected with the RSV-CAT or IL2-CAT reporter plasmids as described in FIGS. 7 and 10, respectively. Plasmid DNA was then isolated from the nuclear pellet following hypotonic lysis of the cells.

Figure 13:
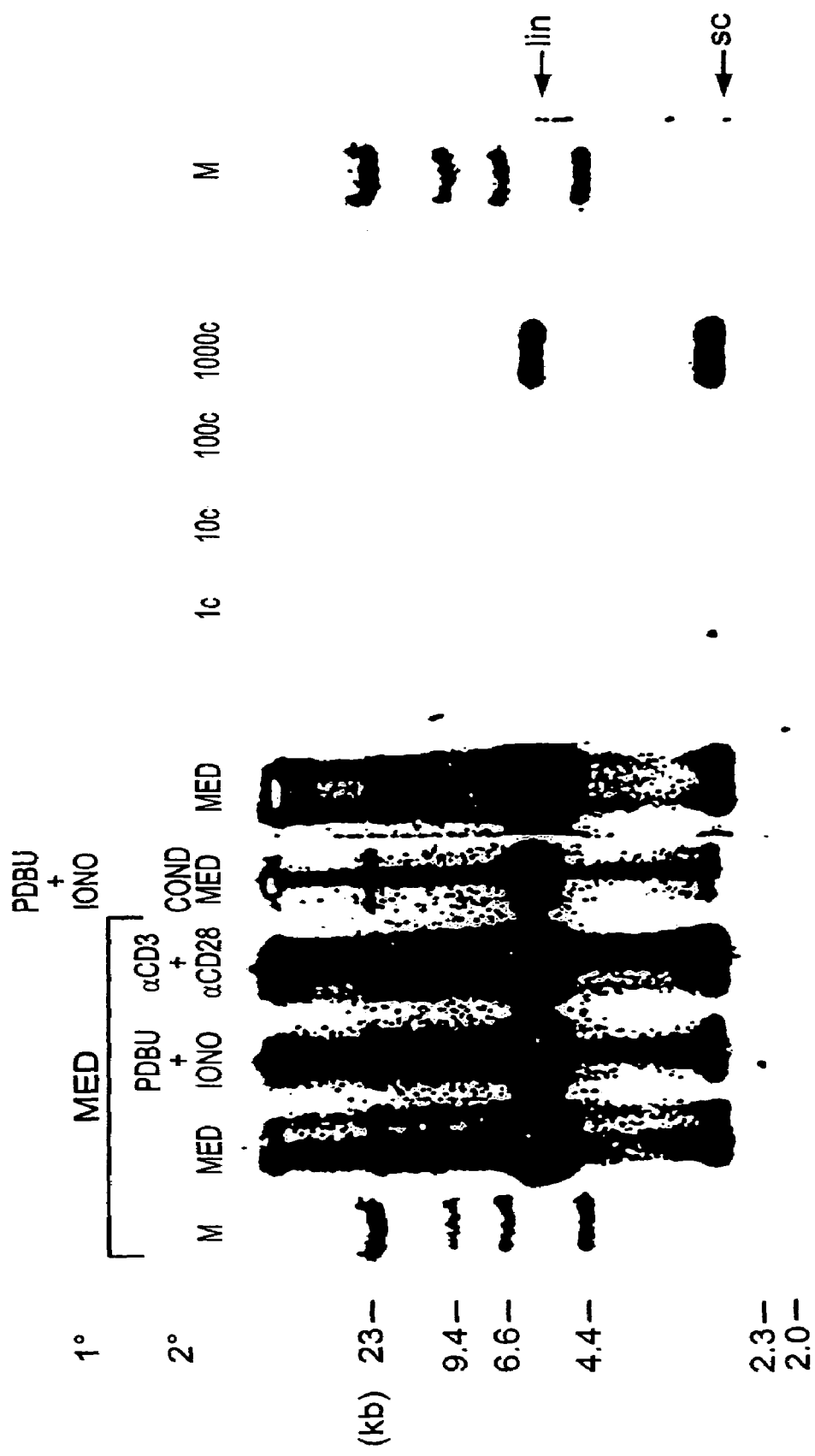
FIG. 13 shows autoradiograms of Southern blots of nuclear DNA extracted from exponentially growing T cells transfected with RSV-CAT and stimulated 10 hours before transfection (1°) with medium alone (MED) or phorbol-12,13-dibutyrate andionomycin (PDBU+IONO) and stimulated 30 hours after transfection (2°) with medium alone (ED), phorbol-12,13-dibutyrate and ionomycin (PDBU+IONO), anti-CD3 and anti-CD28-antibodies (αCD3+αCD28), or conditioned medium (COND MED) and hybridized with an EcoRI fragment from the CAT coding region of RSV-CAT. Plasmid DNA corresponding to 1 (1c), 10 (10c), 100 (100c), and 1000 (1000c) copies of RSV-CAT/cell was used as a control. (lin) linear plasmid; (sc) supercoiled plasmid. M: molecular weight marker.
Figure 14:
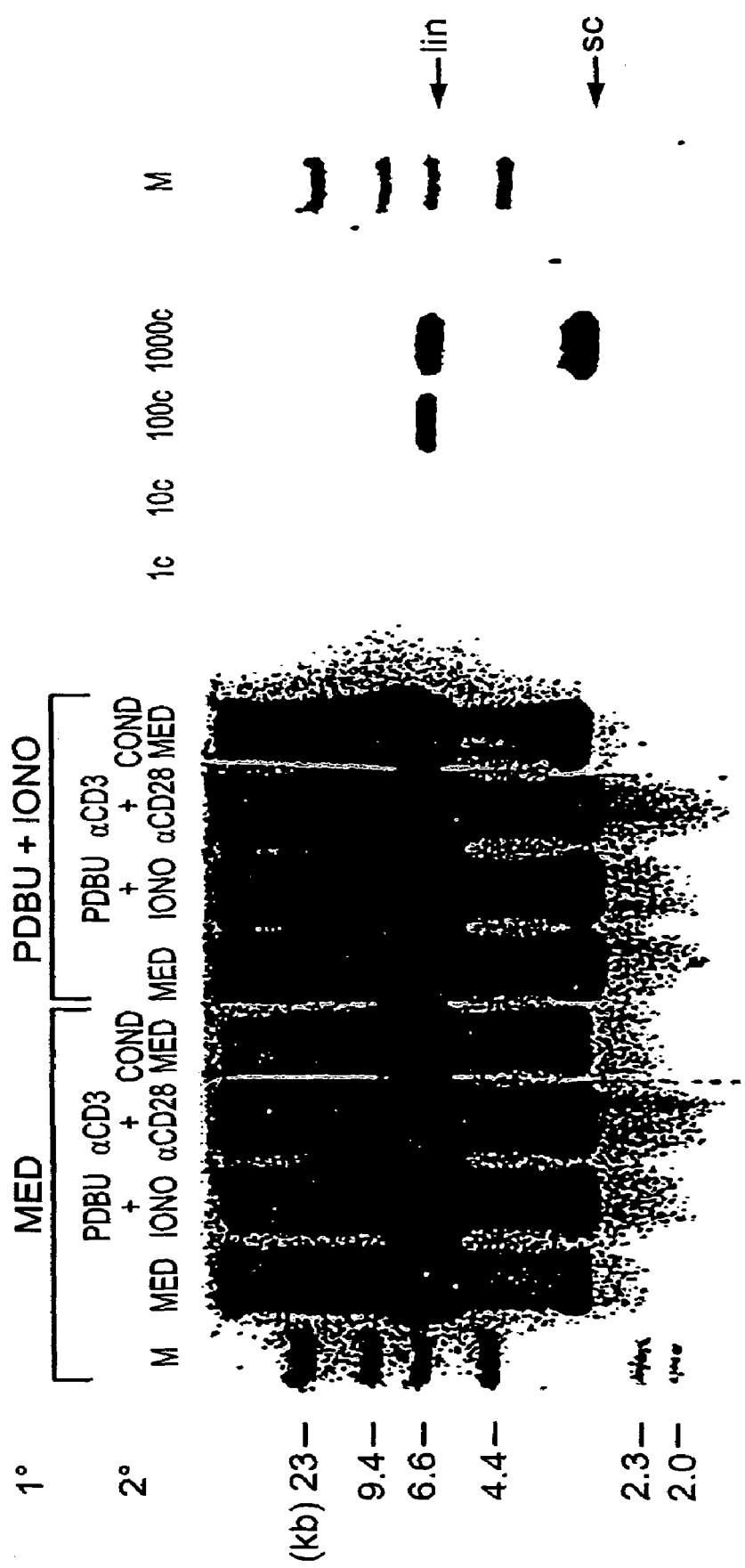
FIG. 14 shows autoradiograms of Southern blots of nuclear DNA extracted from exponentially growing T cells transfected with an IL2-CAT expression construct and stimulated 10 hours before transfection (1°) with media alone (MED) or phorbol-12,13-dibutyrate and ionomycin (PDBU+IONO) and stimulated 30 hours after transfection (2°) with media alone (MED), phorbol-12,13-dibutyrate and ionomycin (PDBU+IONO), anti-CD3 and anti-CD28 antibodies (αCD3+αCD28), or conditioned medium (COND MED) and hybridized with an EcoRI/BamHI fragment from the CAT coding region of IL2-CAT. Plasmid DNA corresponding to 1, 10, 100, and 1000 copies of IL2-CAT/cell was used as a control. (lin) linear plasmid; (sc) supercoiled plasmid. M: molecular weight marker.

As shown in FIGS. 13 and 14, at 40 hours post-transfection, approximately $10^5$ copies/cell of RSV-CAT plasmid were present in the nucleus, representing 10% of the total transfected DNA. As above, there was no appreciable difference in the amount of DNA present in the nuclei of PDBU/IONO prestimulated cells, non-stimulated cells, or the nuclei of cells stimulated after transfection with either PDBU/IONO, αCD3/αCD28, or conditioned medium. Of note, Southern analysis of DNA isolated following hypotonic lysis of cells revealed no evidence of plasmid degradation 40 hours post-transfection.

Having recapitulated the findings using two different methods of DNA isolation, it was still not possible to discount the possibility that the recovery of plasmid DNA was not entirely quantitative. To independently confirm these results, PDBU/IONO prestimulated and non-stimulated cells were transfected with $^{32}$P-radiolabeled linearized RSV-CAT. These cells were then separated into nuclear and cytoplasmic fractions 0, 6, 24, and 48 hours after transfection. The fractions were then counted on a liquid scintillation counter.

Figure 15:
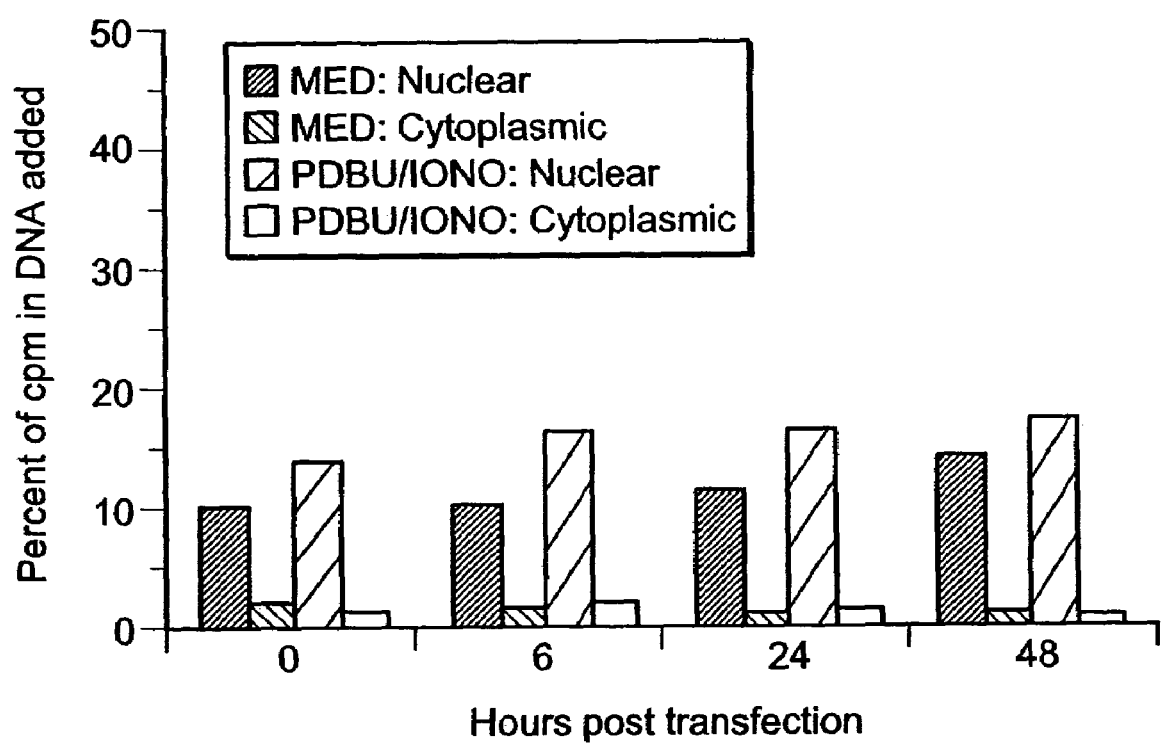
FIG. 15 represents the percentage of counts per minute (cpm) recovered from the nuclei (Nuclear) or cytoplasm (Cytoplasmic) of T cells transfected with $^{32}P$-radiolabeled linearized RSV-CAT and stimulated 10 hours before transfection with phorbol-12,13-dibutyrate and ionomycin (PDBU/IONO) or conditioned medium alone (MED) and harvested immediately (0), 6, 24, or 48 hours following the transfection. The percentage of counts per minute is calculated relative to the total number of counts per minute added to the cells for transfection.

The results, presented in FIG. 15, indicate that within 30 minutes after transfection, 15.2% of the total cpms transfected were taken up by PDBU/IONO prestimulated cells. This compared to 11.9% for non-stimulated cells. Of these counts, 92% were recovered from the nuclear fraction in prestimulated cells and 84% in non-stimulated cells. At subsequent timepoints, the % of total cpm recovered from the nuclear fraction increased from 14.0% at 0 hours to 17.1% at 48 hours in PDBU/IONO prestimulated cells and from 10.0% at 0 hours to 13.9% at 48 hours in non-stimulated cells. This increase in nuclear counts corresponded to a small decrease in the percentage of total cpm recovered in the cytoplasmic fractions of both prestimulated and non-stimulated cells, perhaps reflecting movement of DNA from the cytoplasm to nucleus. However, the small differences in percentage of total cpm recovered from the nuclear fractions of non-signal transduced and PDBU/IONO signal transduced cells cannot account for the dramatic 67- to 345-fold increase in RSV-CAT reporter gene expression between these two populations. Results from counting transfected radiolabeled DNA are in close agreement with Southern blot analysis in terms of both the absolute amount of plasmid entering the cell and the subsequent distribution of that DNA between nuclear and cytoplasmic compartments. In summary, PDBU/IONO prestimulation of cells does not seem to increase reporter gene expression by increasing transfection efficiency or by facilitating the movement of DNA from cytoplasm to nucleus.

Example 6

Superantigen-induced TCR Activation Alters the Nuclear Fate of DNA Containing a Retroviral LTR The above describe examples show that there exist a cellular mechanism, repressible by TCR-mediated signal transduction, which protects quiescent and non-signal transduced proliferating primary T cells from the expression of exogenous DNA in vitro. Given the requirement of TCR-dependent signal transduction for reporter gene expression, it was investigated whether superantigen could serve as a sufficient stimulus for enhanced transgene expression.

Ten hours before transfection, primary human T cells in exponential growth were treated with conditioned medium alone, $5 \times 10^6$ irradiated autologous monocytes, SEA (10 ng/ml), or SEA (10 ng/ml) plus $5 \times 10^6$ irradiated autologous monocytes. Cells were transfected with RSV-CAT or HIV-1-CAT and harvested 40 hours after transfection and assayed for CAT activity.

Figure 16:
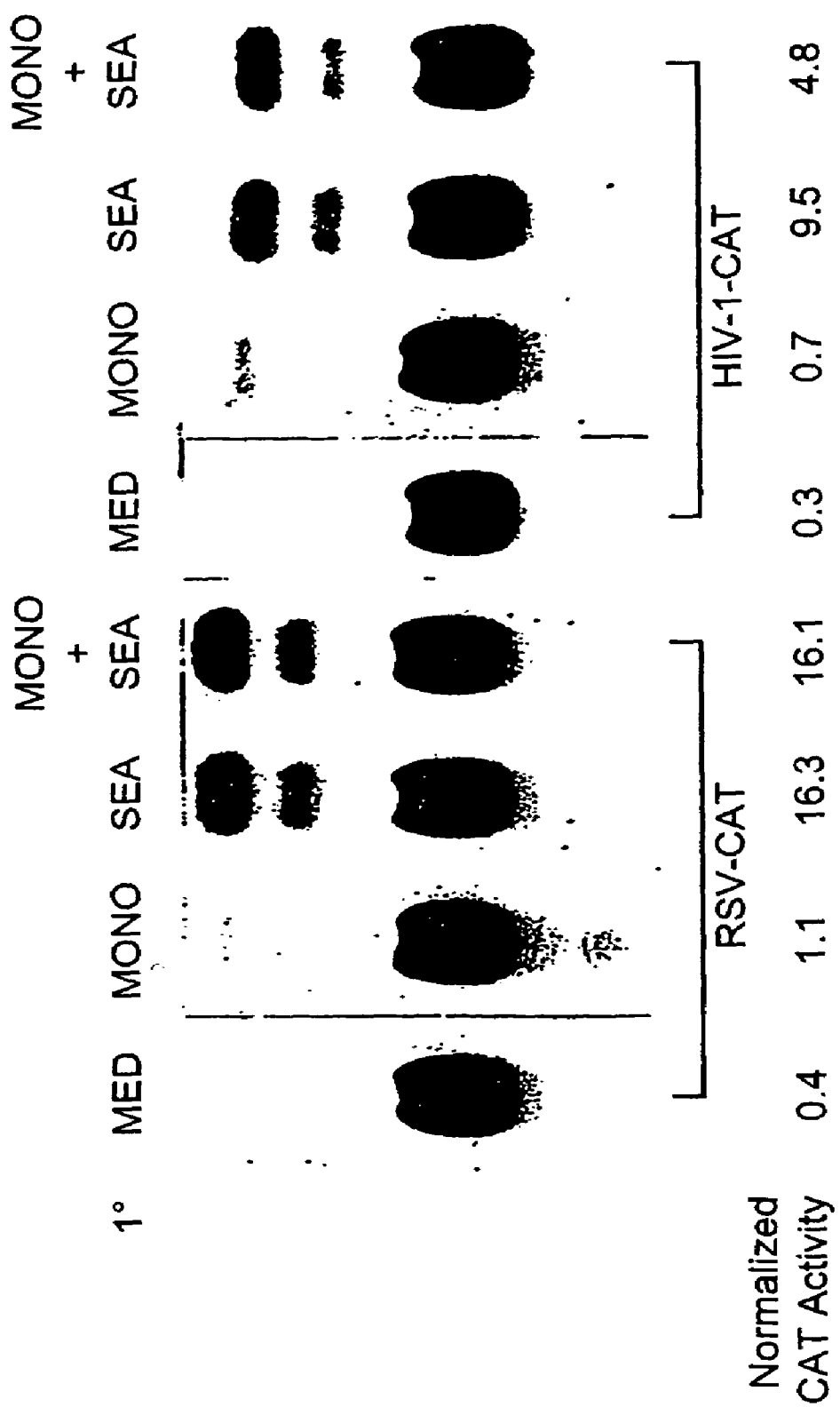
FIG. 16 represents the results of CAT assays performed with cell extracts from proliferating T cells transfected with RSV-CAT or HIV-1-CAT and treated with medium alone (WED), monocytes (MONO), Staphylococcal enterotoxin A (SEA), or moncytes and Staphylococcal enterotoxin A (MONO+SEA) for 10 hours before transfection and harvested 40 hours post transfection. Normalized CAT activity is expressed as (% acetylation/mg protein)×50.

The results of the CAT assays are shown in FIG. 16. In transfections with HIV-1-CAT, PDBU/IONO prestimulation resulted in a 15-fold increase in CAT activity relative to the non-stimulated proliferating control. Coincubation of T cells with $5 \times 10^6$ irradiated autologous monocytes resulted in a small 2.3-fold increase in CAT activity. Treatment with 10 ng/ml SEA resulted in a 32-fold increase in CAT activity, while coincubation of T cells with SEA+$5 \times 10^6$ irradiated autologous monocytes resulted in a 16-fold increase. Therefore, SEA, either alone, or in conjunction with APCs expressing MHC Class II (HLA-DR), increases HIV-1-CAT reporter gene expression. Entirely analogous results are seen in transfections with RSV-CAT (FIG. 16). The proliferative status of SEA and SEA+MONO stimulated cells, as measured by tritiated thymidine incorporation and cell size, was not measurably different from that of non-stimulated proliferating cells. Thus, increased HIV-1-CAT and RSV-CAT reporter expression results from superantigen's effects on signal transduction and not on proliferation per se.

Such a mechanism and its repression may be of great consequence in the events associated with retroviral infection. For example, following the infection of resting T cells by HIV-1, subsequent T cell-activation is required for integration of the HIV-1 genome into the host genome and production of infectious virus (Stevenson, M., Stanwick, T. L., Dempsey, M. P., and Lamonica, C. A. (1990) *EMBO J.* 9(5):1551–1560; Zack, J. A., Arrigo, S. J., Weitsman, S. R., Go,. A. S., Haislip, A., and Chen, I. S. Y. (1990) *Cell* 61:213–222; Bukrinsky, M. L., Stanwick, T. L., Dempsey, M. P., and Stevenson, M. (1991) *Science* 254:423–427). This suggests a model in which HIV-1 persists in a non-productive extrachromosomal state in resting T cells until subsequent antigen or mitogen-induced T cell activation. Recently it has been reported that replication of HIV in resting cells requires tyrosine phosphorylation of the HIV-1 matrix protein (Gallay, P., et al., (1995) *Cell* 80:379).

Superantigens, molecules recognized by T cells expressing specific TCR Vβ gene products, bridge MHC Class II and the TCR, variously leading to cell activation, deletion, or anergy. This group of protein antigensis characterized by its ability to activate large numbers of peripheral blood T cells. Mammalian retroviruses may encode superantigens to block generation of cellular immune reactivity or to facilitate replication consequent to direct cell activation. Recent reports suggest that expression of an HIV-1 superantigen may mediate the T-cell depletion seen in HIV-1 infection (Imberti, L., Sottini, A., Bettiardi, Puoti, M., and Primi, D. (1991) *Science* 254:860–862; Cameron, P. U., Freudentdl, P. S., Barker, J. M., Gezelter, S., Inaba, K., and Steinman, R. M. (1992) *Science* 257:383–387; Laurence, J., Hodtsev, A. S., and Posrnett, D. N. (1992) Int. Conf. AIDS July 19–24; 8(1):Th72; Pantaleo, G., Rebai, N., Graziosi, C., Lane, H. C., Sekaly, R. P., and Fauci, A. S. (1992) Int. Conf. AIDS July 19–24;8(1):Th71). The nature of the signal transduction pathways induced by superantigen activation of T cells remains a matter of controversy (Liu, H., Lampe, M. A., kregui, M. V., and Cantor, H. (1991) *Proc. Natl. Acad. Sci. USA* 88(19):8705–8709; Kanner, S. B., Odum, N., Grosmaire, L., Masewicz, S., Svejgaard, A., and Ledbetter, J. A. (1992) *J. Immunol.* 149(11):3482–3488; Oyaizu, N., Chirmule, N., Yagra, H., Pahwa, R. Good, R. A., and Pahwa, S. (1992) *Proc. Natl. Acad Sci. USA* 89(17):8035–8039). The efficacy of SEA, either alone, or in conjunction with APCS expressing MHC Class II, in increasing either HIV-1-LTR or RSV-LTR driven reporter gene expression in proliferating T cells indicates that superantigen engagement of the TCR may constitute the minimal signal necessary for exogenous DNA to enter an expressible nuclear compartment.

The examples show the existence of an active mechanism, repressible by TCR-mediated signal transduction, which protects quiescent and proliferating T lymphocytes from the expression of exogenous DNA. T cells only express exogenous DNA following signal transduction prior to transfection. This finding has implications in the field of somatic cell gene therapy since cellular proliferation alone may be insufficient for efficient expression of exogenous DNA. Thus, the invention provides a method for efficient expression of a gene introduced in a proliferating T cell. In one embodiment of the invention, T cells are obtained from an individual, stimulated to proliferate ex vivo, genetically transduced by the method of the invention and readministered into the individual. In this particular embodiment, the T cells are contacted with an agent, or a combination of agents, which stimulates T cell receptor mediated signal transduction, such as an anti-CD3 antibody, a combination of phorbol ester and ionomycin, or other agent that bypasses the T cell receptor.

The invention also provides methods for blocking or decreasing expression of exogenous DNA, such as viral DNA. Thus, primary T cells containing exogenous DNA, such as viral DNA, can be stimulated to proliferate while inhibiting viral replication by, for example, stimulating proliferation of the T cells with an agent that does not activate the mechanism required for exogenous gene expression described herein.

Equivalents

Those skilled in the art will recognize, or be able to ascertain using no more than routine experimentation, many equivalents to the specific embodiments of the invention described herein. Such equivalents are intended to be encompassed by the following claims.

The invention claimed is:

1. A method for increasing the expression of an exogenous nucleic acid molecule in T cells, comprising:
   (a) contacting the T cells in vitro with at least one stimulatory agent, wherein the T cells are proliferating prior to contact with the at least one stimulatory agent, thereby forming stimulated proliferating T cells; and
   (b) introducing the exogenous nucleic acid molecule into the T cells from step (a) in vitro, less than 24 hours after contacting of said T cells, wherein the exogenous nucleic acid molecule is introduced into the T cells using a viral vector, provided that the exogenous nucleic acid molecule is not introduced by particle bombardment, such that the expression of the exogenous nucleic acid molecule is increased in the T cells compared with T cells not contacted with the stimulatory agent prior to introducing the exogenous nucleic acid molecule.

2. The method of claim 1, wherein the T cells are contacted in vitro with at least one proliferative agent which stimulates proliferation of the T cells prior to being contacted with the at least one stimulatory agent.

3. The method of claim 1, wherein the T cells are primary T cells.

4. The method of claim 1, wherein the at least one stimulatory agent is a combination of a phorbol ester and a calcium ionophore, a super-antigen, a polyclonal activator, a lymphokine, an antigen presented by an antigen presenting cell, or a protein tyrosine kinase activator.

5. The method of claim 1, wherein the at least one stimulatory agent is an antibody.

6. The method of claim 1, wherein the at least one stimulatory agent is an agent which interacts with the T cell receptor/CD3 complex and provides a primary activation signal to the proliferating T cells.

7. The method of claim 6, wherein the agent which interacts with the T cell receptor/CD3 complex is an agent which interacts with the T cell receptor, an agent which interacts with the CD3 complex, or an agent that stimulates the CD2 complex on T cells.

8. The method of claim 1, wherein the stimulatory agent is an anti-CD3 antibody, or a combination of anti-CD2 antibodies.

9. The method of claim 1, wherein the stimulatory agent is attached to a surface.

10. The method of claim 9, wherein the surface is a bead, a cell surface, or a tissue culture dish.

11. The method of claim 1, wherein the at least one stimulatory agent is a combination of a first agent which provides a primary activation signal to the proliferating T cells, and a second agent which provides a costimulatory signal to the proliferating T cells.

12. The method of claim 11, wherein the first agent is an agent which interacts with the T cell receptor/CD3 complex and provides a primary activation signal to the proliferating T cells.

13. The method of claim 11, wherein the first agent is an anti-CD3 antibody.

14. The method of claim 11, wherein the first agent interacts with a CD2 complex on the T cells.

15. The method of claim 11, wherein the first agent is an antigen on an antigen presenting cell.

16. The method of claim 11, wherein the second agent is an anti-CD28 antibody.

17. The method of claim 11, wherein the second agent is a stimulatory form of a natural ligand of CD28.

18. The method of claim 17, wherein the stimulatory form of a natural ligand of CD28 is the B lymphocyte antigen B7-1.

19. The method of claim 17, wherein the stimulatory form of a natural ligand of CD28 is the B lymphocyte antigen B7-2.

20. The method of claim 11, wherein the first agent or the second agent is attached to a surface.

21. The method of claim 11, wherein the first agent and the second agent are attached to a surface.

22. The method of claim 21, wherein the first agent and the second agent are attached to the same surface.

23. The method of claim 20, wherein the surface is a bead, a cell surface, or a tissue culture dish.

24. The method of claim 1, wherein the viral vector is selected from the group consisting of recombinant retroviruses, adenovirus, adeno-associated virus, and herpes simplex virus-1.

25. The method of claim 1, wherein the viral vector is a recombinant retrovirus.

26. The method of claim 1, wherein the recombinant retrovirus is replication defective.

27. The method of claim 1, wherein said nucleic acid molecule is introduced into said T cells, between approximately 1 hour and less than 24 hours after contacting said T cells in vitro with said at least one stimulatory agent.

28. The method of claim 1, wherein said nucleic acid molecule is introduced into said T cells, approximately 10 hours after contacting said T cells in vitro with said at least one stimulatory agent.

29. The method of claim 1, wherein the T cells of step (b) are further stimulated in vitro to increase their number.

30. The method of claim 1, wherein the T cells are obtained from a subject, and are readministered to the subject after introducing the exogenous nucleic acid molecule into the T cells.

31. A method for increasing the expression of an exogenous nucleic acid molecule in T cells, comprising:
    (a) contacting the T cells with at least one proliferative agent which stimulates proliferation of the T cells, forming proliferating T cells;
    (b) contacting the proliferating T cells in vitro with at least one stimulating agent, thereby forming stimulated proliferating T cells, wherein the at least one stimulatory agent is a combination of a first agent which provides a primary activation signal to the T cells and a second agent which provides a costimulatory signal to the T cells; and
    (c) introducing the exogenous nucleic acid molecule into the T cells from step (b) in vitro, less than 24 hours after contacting of said T cells, wherein the exogenous nucleic acid molecule is introduced into the T cells using a viral vector, provided that the exogenous nucleic acid molecule is not introduced by particle bombardment,
such that the expression of the gene is increased in the T cells compared with T cells not contacted with the stimulatory agent prior to introducing the exogenous nucleic acid molecule.

32. The method of claim 31, wherein the T cells are primary T cells.

33. The method of claim 31, wherein the first agent is an agent which interacts with the T cell receptor/CD3 complex and provides a primary activation signal to the proliferating T cells.

34. The method of claim 33, wherein the first agent is an anti-CD3 antibody.

35. The method of claim 33, wherein the first agent interacts with a CD2 complex on the T cells.

36. The method of claim 33, wherein the first agent is an antigen on an antigen presenting cell.

37. The method of-claim 31, wherein the second agent is an anti-CD28 antibody.

38. The method of claim 31, wherein the second agent is a stimulatory form of a natural ligand of CD28.

39. The method of claim 38, wherein the stimulatory form of a natural ligand of CD28 is the B lymphocyte antigen B7-1 or B7-2.

40. The method of claim 31, wherein the first agent or second agent is an antibody.

41. The method of claim 31, wherein the first agent and the second agent are antibodies.

42. The method of claim 31, wherein the first agent or the second agent is attached to a surface.

43. The method of claim 31, wherein the first agent and the second agent are attached to a surface.

44. The method of claim 43, wherein the surface is a bead, a cell surface, or a tissue culture dish.

45. The method of claim 31, wherein the viral vector is selected from the group consisting of recombinant retroviruses, adenovirus, adeno-associated virus, and herpes simplex virus-1.

46. The method of claim 31, wherein the viral vector is a recombinant retrovirus.

47. The method of claim 31, wherein the recombinant retrovirus is replication defective.

48. The method of claim 31, wherein said nucleic acid molecule is introduced into said T cells, between approximately 1 hour and less than 24 hours after contacting said proliferating T cells in vitro with said at least one stimulatory agent.

49. The method of claim 31, wherein said nucleic acid molecule is introduced into said T cells, approximately 10 hours after contacting said proliferating T cells in vitro with said at least one stimulatory agent.

50. The method of claim 31, wherein the T cells of step (c) are further stimulated in vitro to increase their number.

51. The method of claim 31, wherein the T cells are obtained from a subject and are readministered to the subject after introducing the exogenous nucleic acid molecule into the T cells.

* * * * *

UNITED STATES PATENT AND TRADEMARK OFFICE
CERTIFICATE OF CORRECTION

PATENT NO. : 7,172,869 B2  Page 1 of 1
APPLICATION NO. : 10/828481
DATED : February 6, 2007
INVENTOR(S) : June et al.

It is certified that error appears in the above-identified patent and that said Letters Patent is hereby corrected as shown below:

Column 28, lines 12-14, please delete the text "provided that the exogenous nucleic acid molecule is not introduced by particle bombardment,"

Column 29, lines 53-55, please delete the text "provided that the exogenous nucleic acid molecule is not introduced by particle bombardment,"

Signed and Sealed this

Seventh Day of August, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,172,869 B2 | Page 1 of 1 |
| APPLICATION NO. | : 10/828481 | |
| DATED | : February 6, 2007 | |
| INVENTOR(S) | : Carl H. June et al. | |

It is certified that error appears in the above-identified patent and that said Letters Patent is hereby corrected as shown below:

Title Page, Item (75), delete "Thompson B. Craig" and insert --Craig B. Thompson--.

Signed and Sealed this

Eighteenth Day of September, 2007

JON W. DUDAS
*Director of the United States Patent and Trademark Office*